(12) United States Patent
Kramer et al.

(10) Patent No.: US 12,741,095 B2
(45) Date of Patent: Sep. 22, 2026

(54) NEEDLE ASSISTED INJECTION DEVICE HAVING REDUCED TRIGGER FORCE

(71) Applicant: Antares Pharma, Inc., Ewing, NJ (US)

(72) Inventors: Thomas Kramer, Andover, MN (US); Matthew H. Rust, Hudson, WI (US); Paul M. Goudreau, St. Paul, MN (US); Peter A. Hoeft, Seattle, WA (US); Julius C. Sund, Plymouth, MN (US); Peter L. Sadowski, Woodbury, MN (US); Michael Travanty, S. Minneapolis, MN (US); Patrick Madsen, Litchfield, MN (US)

(73) Assignee: Antares Pharma, Inc., Ewing, NJ (US)

( * ) Notice: Subject to any disclaimer, the term of this patent is extended or adjusted under 35 U.S.C. 154(b) by 0 days.

(21) Appl. No.: 19/352,067

(22) Filed: Oct. 7, 2025

(65) Prior Publication Data

US 2026/0034302 A1 Feb. 5, 2026

Related U.S. Application Data

(63) Continuation of application No. 18/927,653, filed on Oct. 25, 2024, which is a continuation of application (Continued)

(51) Int. Cl.
*A61M 5/20* (2006.01)
*A61M 5/30* (2006.01)

(Continued)

(52) U.S. Cl.
CPC ............ *A61M 5/2033* (2013.01); *A61M 5/20* (2013.01); *A61M 5/2053* (2013.01); *A61M 5/30* (2013.01);

(Continued)

(58) Field of Classification Search
CPC .... A61M 5/2033; A61M 5/20; A61M 5/2053; A61M 5/30; A61M 5/5086; A61M 5/326;

(Continued)

(56) References Cited

U.S. PATENT DOCUMENTS

| | | | |
|---|---|---|---|
| 547,370 | A | 10/1895 | Chalefou |
| 1,465,793 | A | 8/1923 | Schilling |

(Continued)

FOREIGN PATENT DOCUMENTS

| | | |
|---|---|---|
| AR | 00081651 | 10/2012 |
| AR | 082053 | 11/2012 |

(Continued)

OTHER PUBLICATIONS

"Skin", American Medical Association (AMA) Current Procedural Terminology, 1998, http://www.ama-assn.org/ama/pub/category/print/7176. html, 1 page.

(Continued)

*Primary Examiner* — James D Ponton
(74) *Attorney, Agent, or Firm* — Morgan, Lewis & Bockius LLP

(57) ABSTRACT

An exemplary embodiment of an injector includes a trigger mechanism, an energy source, and a user-operable firing-initiation member. The trigger mechanism can include a floating trigger member having a retaining portion, a ram assembly having a ram configured to pressurize a medicament container for expelling a medicament therefrom, the ram assembly further having a floating trigger engagement member configured to engage the retaining portion of the floating trigger member when the floating trigger member is in a pre-firing condition. The energy source can be associated with the ram for powering the ram to expel the medicament, and the user-operable firing-initiation member can be operable for causing an axial rotation of the floating (Continued)

trigger member from the pre-firing condition to a firing condition in which the floating trigger engagement member is released from the retaining portion to allow the energy source to fire the ram.

16 Claims, 13 Drawing Sheets

Related U.S. Application Data

No. 17/819,171, filed on Aug. 11, 2022, now Pat. No. 12,220,560, which is a continuation of application No. 16/436,377, filed on Jun. 10, 2019, now Pat. No. 11,446,440, which is a continuation of application No. 15/155,804, filed on May 16, 2016, now Pat. No. 10,357,609, which is a continuation of application No. 13/889,190, filed on May 7, 2013, now Pat. No. 9,364,611.

(60) Provisional application No. 61/776,283, filed on Mar. 11, 2013, provisional application No. 61/763,395, filed on Feb. 11, 2013, provisional application No. 61/643,845, filed on May 7, 2012, provisional application No. 61/643,659, filed on May 7, 2012.

(51) Int. Cl.
*A61M 5/31* (2006.01)
*A61M 5/32* (2006.01)
*A61M 5/50* (2006.01)

(52) U.S. Cl.
CPC ... *A61M 5/5086* (2013.01); *A61M 2005/2013* (2013.01); *A61M 2005/2026* (2013.01); *A61M 2005/208* (2013.01); *A61M 2005/3125* (2013.01); *A61M 5/326* (2013.01); *A61M 2202/0007* (2013.01); *A61M 2202/048* (2013.01)

(58) Field of Classification Search
CPC .. A61M 2005/2013; A61M 2005/2026; A61M 2005/208; A61M 2005/3125; A61M 2202/0007; A61M 2202/048
See application file for complete search history.

(56) References Cited

U.S. PATENT DOCUMENTS 1,512,294 A 10/1924 Marcy
1,687,323 A 10/1928 Cook
2,354,649 A 8/1944 Bruckner
2,607,344 A 8/1952 Brown
2,645,223 A 7/1953 Lawshe
2,648,334 A 8/1953 Brown
2,687,730 A 8/1954 Hein
2,688,967 A 9/1954 Huber
2,699,166 A 1/1955 Bickinson
2,717,601 A 9/1955 Brown
2,728,341 A 12/1955 Roehr
2,737,946 A 3/1956 Hein, Jr.
2,813,528 A 11/1957 Blackman
2,866,458 A 12/1958 Mesa et al.
2,888,924 A 6/1959 Dunmire
2,893,390 A 7/1959 Lockhart
3,130,724 A 4/1964 Higgins
3,166,069 A 1/1965 Enstrom
3,375,825 A 4/1968 Keller
3,382,865 A 5/1968 Worrall
3,526,225 A 9/1970 Hayamamachi
3,557,784 A 1/1971 Shields
3,563,098 A 2/1971 Gley
3,605,744 A 9/1971 Dwyer
3,688,765 A 9/1972 Gasaway
3,702,609 A 11/1972 Steiner
3,712,301 A 1/1973 Sarnoff
3,742,948 A 7/1973 Post et al.
3,770,026 A 11/1973 Isenberg
3,790,048 A 2/1974 Luciano et al.
3,797,489 A 3/1974 Sarnoff
3,797,491 A 3/1974 Hurschman
3,811,441 A 5/1974 Sarnoff
3,831,814 A 8/1974 Butler
3,848,593 A 11/1974 Baldwin
3,882,863 A 5/1975 Sarnoff et al.
3,892,237 A 7/1975 Steiner
3,895,633 A 7/1975 Bartner et al.
3,946,732 A 3/1976 Hurscham
4,031,893 A 6/1977 Kaplan et al.
4,067,333 A 1/1978 Reinhardt et al.
4,127,118 A 11/1978 Latorre
4,171,698 A 10/1979 Genese
4,222,392 A 9/1980 Brennan
4,227,528 A 10/1980 Wardlaw
4,258,713 A 3/1981 Wardlaw
4,282,986 A 8/1981 af Ekenstam et al.
4,316,463 A 2/1982 Schmitz et al.
4,316,643 A 2/1982 Burk et al.
4,328,802 A 5/1982 Curley et al.
4,333,456 A 6/1982 Webb
4,333,458 A 6/1982 Margulies et al.
4,338,980 A 7/1982 Schwebel et al.
4,373,526 A 2/1983 Kling
4,378,015 A 3/1983 Wardlaw
4,411,661 A 10/1983 Kersten
4,484,910 A 11/1984 Sarnoff et al.
4,529,403 A 7/1985 Kamstra
4,553,962 A 11/1985 Brunet
4,558,690 A 12/1985 Joyce
4,573,971 A 3/1986 Kamstra
4,592,745 A 6/1986 Rex et al.
4,624,660 A 11/1986 Mijers et al.
4,634,027 A 1/1987 Kanarvogel
4,661,098 A 4/1987 Bekkering et al.
4,662,878 A 5/1987 Lindmayer
4,664,653 A 5/1987 Sagstetter et al.
4,664,655 A 5/1987 Orentreich et al.
4,678,461 A 7/1987 Mesa
4,719,825 A 1/1988 LaHaye et al.
4,722,728 A 2/1988 Dixon
4,774,772 A 10/1988 Vetter et al.
4,790,824 A 12/1988 Morrow et al.
4,818,517 A 4/1989 Kwee et al.
4,820,286 A 4/1989 van der Wal
4,822,340 A 4/1989 Kamstra
4,830,217 A 5/1989 Dufresne et al.
4,874,381 A 10/1989 Vetter
4,883,472 A 11/1989 Michel
4,913,699 A 4/1990 Parsons
4,915,701 A 4/1990 Halkyard
4,929,238 A 5/1990 Baum
4,936,833 A 6/1990 Sams
4,940,460 A 7/1990 Casey et al.
4,966,581 A 10/1990 Landau
4,968,302 A 11/1990 Schluter et al.
4,973,318 A 11/1990 Holm et al.
4,976,701 A 12/1990 Ejlersen et al.
4,982,769 A 1/1991 Fournier et al.
4,986,816 A 1/1991 Steiner et al.
5,042,977 A 8/1991 Bechtold et al.
5,062,830 A 11/1991 Dunlap
5,064,413 A 11/1991 McKinnon et al.
5,069,670 A 12/1991 Vetter et al.
5,078,680 A 1/1992 Sarnoff
5,080,648 A 1/1992 D'Antonio
5,080,649 A 1/1992 Vetter
5,085,641 A 2/1992 Sarnoff et al.
5,085,642 A 2/1992 Sarnoff et al.
5,092,842 A 3/1992 Bechtold et al.
5,102,388 A 4/1992 Richmond
5,102,393 A 4/1992 Sarnoff et al.
5,104,380 A 4/1992 Holman et al.

(56) References Cited

U.S. PATENT DOCUMENTS 5,114,406 A 5/1992 Gabriel et al.
5,137,516 A 8/1992 Rand et al.
5,137,528 A 8/1992 Crose
5,139,490 A 8/1992 Vetter et al.
5,163,907 A 11/1992 Szuszkiewicz
5,176,643 A 1/1993 Kramer et al.
5,180,370 A 1/1993 Gillespie
5,185,985 A 2/1993 Vetter et al.
5,195,983 A 3/1993 Boese
5,221,348 A 6/1993 Masano
5,226,895 A 7/1993 Harris
5,232,459 A 8/1993 Hjertman
5,256,142 A 10/1993 Colavecchio
5,263,934 A 11/1993 Haak
5,271,744 A 12/1993 Kramer et al.
5,279,543 A 1/1994 Glikfeld et al.
5,279,576 A 1/1994 Loo et al.
5,279,585 A 1/1994 Balkwill
5,279,586 A 1/1994 Balkwill
5,281,198 A 1/1994 Haber et al.
5,290,228 A 3/1994 Uemura et al.
5,295,965 A 3/1994 Wilmot
5,300,030 A 4/1994 Crossman et al.
5,304,128 A 4/1994 Haber et al.
5,304,152 A 4/1994 Sams
5,308,341 A 5/1994 Chanoch
5,318,522 A 6/1994 D'Antonio
5,320,603 A 6/1994 Vetter et al.
5,330,431 A 7/1994 Herskowitz
5,332,399 A 7/1994 Grabenkort et al.
5,334,144 A 8/1994 Alchas et al.
5,342,308 A 8/1994 Boschetti
5,350,367 A 9/1994 Stiehl et al.
5,354,286 A 10/1994 Mesa et al.
5,358,489 A 10/1994 Wyrick
RE34,845 E 1/1995 Vetter et al.
5,391,151 A 2/1995 Wilmot
5,405,362 A 4/1995 Kramer et al.
5,415,648 A 5/1995 Malay et al.
5,425,715 A 6/1995 Dalling et al.
5,451,210 A 9/1995 Kramer et al.
5,478,316 A 12/1995 Bitdinger et al.
5,505,694 A 4/1996 Hubbard et al.
5,514,097 A 5/1996 Knauer
5,514,107 A 5/1996 Haber et al.
5,540,664 A 7/1996 Wyrick
5,542,760 A 8/1996 Chanoch et al.
5,544,234 A 8/1996 Terajima et al.
5,549,561 A 8/1996 Hjertman
5,554,134 A 9/1996 Bonnichsen
5,562,625 A 10/1996 Stefancin, Jr.
5,567,160 A 10/1996 Massino
5,569,190 A 10/1996 D'Antonio
5,569,192 A 10/1996 van der Wal
5,569,236 A 10/1996 Kriesel
5,573,042 A 11/1996 De Haen
5,593,388 A 1/1997 Phillips
5,599,302 A 2/1997 Lilley et al.
5,599,309 A 2/1997 Marshall et al.
5,605,542 A 2/1997 Tanaka et al.
5,637,094 A 6/1997 Stewart, Jr. et al.
5,637,100 A 6/1997 Sudo
5,649,912 A 7/1997 Peterson
5,658,259 A 8/1997 Pearson et al.
5,665,071 A 9/1997 Wyrick
5,688,251 A 11/1997 Chanoch
5,695,472 A 12/1997 Wyrick
5,704,911 A 1/1998 Parsons
5,725,508 A 3/1998 Chanoch et al.
5,730,723 A 3/1998 Castellano et al.
5,743,889 A 4/1998 Sams
5,769,138 A 6/1998 Sadowski et al.
5,785,691 A 7/1998 Vetter et al.
5,788,670 A 8/1998 Reinhard et al.
5,801,057 A 9/1998 Smart et al.
5,807,309 A 9/1998 Lundquist et al.
5,820,602 A 10/1998 Kovelman et al.
5,820,622 A 10/1998 Gross et al.
5,827,232 A 10/1998 Chanoch et al.
5,836,911 A 11/1998 Marzynski et al.
5,843,036 A 12/1998 Olive et al.
5,846,233 A 12/1998 Lilley et al.
5,851,197 A 12/1998 Marano et al.
5,851,198 A 12/1998 Castellano et al.
5,860,456 A 1/1999 Bydlon et al.
5,865,795 A 2/1999 Schiff et al.
5,865,799 A 2/1999 Tanaka et al.
5,868,711 A 2/1999 Kramer et al.
5,873,857 A 2/1999 Kriesel
5,875,976 A 3/1999 Nelson et al.
5,879,327 A 3/1999 DeFarges et al.
5,891,085 A 4/1999 Lilley et al.
5,891,086 A 4/1999 Weston
5,893,842 A 4/1999 Imbert
5,919,159 A 7/1999 Lilley et al.
5,921,966 A 7/1999 Bendek et al.
5,925,017 A 7/1999 Kriesel et al.
5,928,205 A 7/1999 Marshall
5,935,949 A 8/1999 White
5,951,528 A 9/1999 Parkin
5,957,897 A 9/1999 Jeffrey
5,960,797 A 10/1999 Kramer et al.
5,989,227 A 11/1999 Vetter et al.
6,004,297 A 12/1999 Steenfeldt-Jensen et al.
6,045,534 A 4/2000 Jacobson et al.
6,056,716 A 5/2000 D'Antonio et al.
6,077,247 A 6/2000 Marshall et al.
6,083,201 A 7/2000 Skinkle
6,090,070 A 7/2000 Hager et al.
6,099,504 A 8/2000 Gross et al.
6,123,684 A 9/2000 Deboer et al.
6,132,395 A 10/2000 Landau et al.
6,159,181 A 12/2000 Crossman et al.
6,171,276 B1 1/2001 Lippe et al.
6,203,529 B1 3/2001 Gabriel et al.
6,210,369 B1 4/2001 Wilmot et al.
6,221,046 B1 4/2001 Burroughs et al.
6,221,053 B1 4/2001 Walters et al.
6,223,408 B1 5/2001 Vetter et al.
6,231,540 B1 5/2001 Smedegaard
6,241,709 B1 6/2001 Bechtold et al.
6,245,347 B1 6/2001 Zhang et al.
6,258,078 B1 7/2001 Thilly
6,264,629 B1 7/2001 Landau
6,270,479 B1 8/2001 Bergens et al.
6,309,371 B1 10/2001 Deboer et al.
6,319,224 B1 11/2001 Stout et al.
6,371,939 B2 4/2002 Bergens et al.
6,383,168 B1 5/2002 Landau et al.
6,391,003 B1 5/2002 Lesch, Jr.
6,406,456 B1 6/2002 Slate et al.
6,428,528 B2 8/2002 Sadowski et al.
6,471,669 B2 10/2002 Landau
6,494,865 B1 12/2002 Alchas
6,517,517 B1 2/2003 Farrugia et al.
6,530,904 B1 3/2003 Edwards et al.
6,544,234 B1 4/2003 Gabriel
6,562,006 B1 5/2003 Hjertman et al.
6,565,553 B2 5/2003 Sadowski et al.
6,568,259 B2 5/2003 Saheki et al.
6,569,123 B2 5/2003 Alchas et al.
6,569,143 B2 5/2003 Alchas et al.
6,584,910 B1 7/2003 Plass
6,589,210 B1 7/2003 Rolfe
6,607,508 B2 8/2003 Knauer
6,620,137 B2 9/2003 Kirchhofer et al.
6,641,561 B1 11/2003 Hill et al.
6,645,170 B2 11/2003 Landau
6,656,150 B2 12/2003 Hill et al.
6,673,035 B1 1/2004 Rice et al.
6,682,504 B2 1/2004 Nelson et al.
6,689,092 B2 2/2004 Zierenberg et al.
6,706,000 B2 3/2004 Perez et al.
6,746,429 B2 6/2004 Sadowski et al.

(56) References Cited

U.S. PATENT DOCUMENTS 6,767,336 B1 7/2004 Kaplan
6,805,686 B1 10/2004 Fathallah et al.
6,830,560 B1 12/2004 Gross et al.
6,899,698 B2 5/2005 Sams
6,932,793 B1 8/2005 Marshall et al.
6,932,794 B2 8/2005 Giambattista et al.
6,936,032 B1 8/2005 Bush, Jr. et al.
6,969,370 B2 11/2005 Langley et al.
6,969,372 B1 11/2005 Halseth
6,979,316 B1 12/2005 Rubin et al.
6,986,758 B2 1/2006 Schiffmann
6,997,901 B2 2/2006 Popovsky
7,018,364 B2 3/2006 Giambattista et al.
7,044,125 B2 5/2006 Vedrine et al.
7,066,907 B2 6/2006 Crossman et al.
7,112,187 B2 9/2006 Karlsson
7,118,552 B2 10/2006 Shaw et al.
7,118,553 B2 10/2006 Scherer
7,169,132 B2 1/2007 Bendek et al.
7,195,616 B2 3/2007 Diller et al.
7,218,962 B2 5/2007 Freyman
7,220,247 B2 5/2007 Shaw et al.
7,247,149 B2 7/2007 Beyerlein
7,291,132 B2 11/2007 DeRuntz et al.
7,292,885 B2 11/2007 Scott et al.
7,297,136 B2 11/2007 Wyrick
7,341,575 B2 3/2008 Rice et al.
7,361,160 B2 4/2008 Hommann et al.
7,390,314 B2 6/2008 Stutz, Jr. et al.
7,390,319 B2 6/2008 Friedman
7,407,492 B2 8/2008 Gurtner
7,416,540 B2 8/2008 Edwards et al.
7,442,185 B2 10/2008 Amark et al.
7,449,012 B2 11/2008 Young et al.
7,488,308 B2 2/2009 Lesch, Jr.
7,488,313 B2 2/2009 Segal et al.
7,488,314 B2 2/2009 Segal et al.
7,500,964 B2 3/2009 Shaw et al.
7,517,342 B2 4/2009 Scott et al.
7,519,418 B2 4/2009 Scott et al.
7,544,188 B2 6/2009 Edwards et al.
7,547,293 B2 6/2009 Williamson et al.
7,569,035 B1 8/2009 Wilmot et al.
7,611,491 B2 11/2009 Pickhard
7,621,887 B2 11/2009 Griffiths et al.
7,621,891 B2 11/2009 Wyrick
7,635,348 B2 12/2009 Raven et al.
7,635,350 B2 12/2009 Scherer
7,637,891 B2 12/2009 Wall
7,648,482 B2 1/2010 Edwards et al.
7,648,483 B2 1/2010 Edwards et al.
7,654,983 B2 2/2010 De La Sema et al.
7,658,724 B2 2/2010 Rubin et al.
7,670,314 B2 3/2010 Wall et al.
7,704,237 B2 4/2010 Fisher et al.
7,717,877 B2 5/2010 Lavi et al.
7,722,595 B2 5/2010 Pettis et al.
7,731,686 B2 6/2010 Edwards et al.
7,731,690 B2 6/2010 Edwards et al.
7,736,333 B2 6/2010 Gillespie, III
7,744,582 B2 6/2010 Sadowski et al.
7,749,194 B2 7/2010 Edwards et al.
7,749,195 B2 7/2010 Hommann
7,762,996 B2 7/2010 Palasis
7,776,015 B2 8/2010 Sadowski et al.
7,794,432 B2 9/2010 Young et al.
7,811,254 B2 10/2010 Wilmot et al.
7,862,543 B2 1/2011 Potter et al.
7,896,841 B2 3/2011 Wall et al.
7,901,377 B1 3/2011 Harrison et al.
7,905,352 B2 3/2011 Wyrick
7,905,866 B2 3/2011 Haider et al.
7,918,823 B2 4/2011 Edwards et al.
7,927,303 B2 4/2011 Wyrick
7,931,618 B2 4/2011 Wyrick
7,947,017 B2 5/2011 Edwards et al.
RE42,463 E 6/2011 Landau
7,955,304 B2 6/2011 Guillermo
7,967,772 B2 6/2011 McKenzie et al.
7,988,675 B2 8/2011 Gillespie, III et al.
8,016,774 B2 9/2011 Freeman et al.
8,016,788 B2 9/2011 Edwards et al.
8,021,335 B2 9/2011 Lesch, Jr.
8,048,035 B2 11/2011 Mesa et al.
8,048,037 B2 11/2011 Kohlbrenner et al.
8,057,427 B2 11/2011 Griffiths et al.
8,066,659 B2 11/2011 Joshi et al.
8,083,711 B2 12/2011 Enggaard
8,100,865 B2 1/2012 Spofforth
8,105,272 B2 1/2012 Williamson et al.
8,105,281 B2 1/2012 Edwards et al.
8,110,209 B2 2/2012 Prestrelski et al.
8,123,719 B2 2/2012 Edwards et al.
8,123,724 B2 2/2012 Gillespie, III
8,162,873 B2 4/2012 Muto et al.
8,162,886 B2 4/2012 Sadowski et al.
8,167,840 B2 5/2012 Matusch
8,167,866 B2 5/2012 Klein
8,177,758 B2 5/2012 Brooks, Jr. et al.
8,187,224 B2 5/2012 Wyrick
8,216,180 B2 7/2012 Tschirren et al.
8,216,192 B2 7/2012 Burroughs et al.
8,226,618 B2 7/2012 Geertsen
8,226,631 B2 7/2012 Boyd et al.
8,233,135 B2 7/2012 Jansen et al.
8,235,952 B2 8/2012 Wikner
8,246,577 B2 8/2012 Schrul et al.
8,251,947 B2 8/2012 Kramer et al.
8,257,318 B2 9/2012 Thogersen et al.
8,257,319 B2 9/2012 Plumptre
8,267,899 B2 9/2012 Moller
8,267,900 B2 9/2012 Harms et al.
8,273,798 B2 9/2012 Bausch et al.
8,275,454 B2 9/2012 Adachi et al.
8,276,583 B2 10/2012 Farieta et al.
8,277,412 B2 10/2012 Kronestedt
8,277,413 B2 10/2012 Kirchhofer
8,298,175 B2 10/2012 Hirschel et al.
8,298,194 B2 10/2012 Moller
8,300,852 B2 10/2012 Terada
RE43,834 E 11/2012 Steenfeldt-Jensen et al.
8,308,232 B2 11/2012 Zamperla et al.
8,308,695 B2 11/2012 Laiosa
8,313,466 B2 11/2012 Edwards et al.
8,317,757 B2 11/2012 Plumptre
8,323,237 B2 12/2012 Radmer et al.
8,333,739 B2 12/2012 Moller
8,337,472 B2 12/2012 Edginton et al.
8,343,103 B2 1/2013 Moser
8,343,109 B2 1/2013 Marshall et al.
8,348,905 B2 1/2013 Radmer et al.
8,353,878 B2 1/2013 Moller et al.
8,357,120 B2 1/2013 Moller et al.
8,357,125 B2 1/2013 Grunhut et al.
8,361,036 B2 1/2013 Moller et al.
8,366,680 B2 2/2013 Raab
8,372,031 B2 2/2013 Elmen et al.
8,372,042 B2 2/2013 Wieselblad
8,376,993 B2 2/2013 Cox et al.
8,398,593 B2 3/2013 Eich et al.
8,409,149 B2 4/2013 Hommann et al.
8,435,215 B2 5/2013 Arby et al.
8,496,619 B2 7/2013 Kramer
9,364,610 B2 6/2016 Kramer
9,364,611 B2 * 6/2016 KraMer ............. A61M 5/2033
9,446,195 B2 9/2016 Kramer
11,446,440 B2 9/2022 Kramer
2001/0039394 A1 11/2001 Weston
2001/0049496 A1 12/2001 Kirchhofer et al.
2002/0007149 A1 1/2002 Nelson et al.
2002/0045866 A1 4/2002 Sadowski et al.
2002/0173752 A1 11/2002 Polzin
2002/0183690 A1 12/2002 Arnisolle
2002/0188251 A1 12/2002 Staylor et al.

(56) References Cited

U.S. PATENT DOCUMENTS

| | | | |
|---|---|---|---|
| 2003/0040697 | A1 | 2/2003 | Pass et al. |
| 2003/0083621 | A1 | 5/2003 | Shaw et al. |
| 2003/0105430 | A1 | 6/2003 | Lavi et al. |
| 2003/0130619 | A1 | 7/2003 | Safabash et al. |
| 2003/0158523 | A1 | 8/2003 | Hjertman et al. |
| 2003/0171717 | A1 | 9/2003 | Farrugia et al. |
| 2003/0229330 | A1 | 12/2003 | Hickle |
| 2003/0236502 | A1 | 12/2003 | De La Serna et al. |
| 2004/0039336 | A1 | 2/2004 | Amark et al. |
| 2004/0039337 | A1 | 2/2004 | Letzing |
| 2004/0097783 | A1 | 5/2004 | Peters et al. |
| 2004/0097883 | A1 | 5/2004 | Roe |
| 2004/0143213 | A1 | 7/2004 | Hunter et al. |
| 2004/0220524 | A1 | 11/2004 | Sadowski et al. |
| 2004/0267207 | A1 | 12/2004 | Veasey et al. |
| 2004/0267355 | A1 | 12/2004 | Scott et al. |
| 2005/0020979 | A1 | 1/2005 | Westbye et al. |
| 2005/0027255 | A1 | 2/2005 | Lavi et al. |
| 2005/0033234 | A1 | 2/2005 | Sadowski et al. |
| 2005/0080377 | A1 | 4/2005 | Sadowski et al. |
| 2005/0101919 | A1 | 5/2005 | Brunnberg |
| 2005/0165360 | A1 | 7/2005 | Stamp |
| 2005/0165363 | A1 | 7/2005 | Judson et al. |
| 2005/0209569 | A1 | 9/2005 | Ishikawa et al. |
| 2005/0215955 | A1 | 9/2005 | Slawson |
| 2005/0240145 | A1 | 10/2005 | Scott et al. |
| 2005/0256499 | A1 | 11/2005 | Pettis et al. |
| 2005/0261634 | A1 | 11/2005 | Karlsson |
| 2005/0273054 | A1 | 12/2005 | Asch |
| 2006/0025747 | A1 | 2/2006 | Sullivan et al. |
| 2006/0030819 | A1* | 2/2006 | Young ............... A61M 5/31596 604/187 |
| 2006/0106362 | A1 | 5/2006 | Pass et al. |
| 2006/0129122 | A1 | 6/2006 | Wyrick |
| 2006/0224124 | A1 | 10/2006 | Scherer |
| 2006/0258988 | A1 | 11/2006 | Keitel et al. |
| 2006/0258990 | A1 | 11/2006 | Weber |
| 2007/0017533 | A1 | 1/2007 | Wyrick |
| 2007/0025890 | A1 | 2/2007 | Joshi et al. |
| 2007/0027430 | A1 | 2/2007 | Hommann |
| 2007/0088288 | A1 | 4/2007 | Barron et al. |
| 2007/0093775 | A1 | 4/2007 | Daly |
| 2007/0100288 | A1 | 5/2007 | Bozeman et al. |
| 2007/0123818 | A1 | 5/2007 | Griffiths et al. |
| 2007/0123829 | A1 | 5/2007 | Atterbury et al. |
| 2007/0129686 | A1 | 6/2007 | Daily et al. |
| 2007/0129687 | A1 | 6/2007 | Marshall et al. |
| 2007/0185432 | A1 | 8/2007 | Etheredge et al. |
| 2007/0191784 | A1 | 8/2007 | Jacobs et al. |
| 2007/0219498 | A1 | 9/2007 | Malone et al. |
| 2008/0059133 | A1 | 3/2008 | Edwards et al. |
| 2008/0154199 | A1 | 6/2008 | Wyrick |
| 2008/0154200 | A1 | 6/2008 | Lesch |
| 2008/0185069 | A1 | 8/2008 | Clark |
| 2008/0262427 | A1 | 10/2008 | Hommann |
| 2008/0262436 | A1 | 10/2008 | Olson |
| 2008/0262445 | A1 | 10/2008 | Hsu et al. |
| 2009/0124981 | A1 | 5/2009 | Evans |
| 2009/0124997 | A1 | 5/2009 | Pettis et al. |
| 2009/0204062 | A1 | 8/2009 | Muto et al. |
| 2009/0254027 | A1 | 10/2009 | Moller |
| 2009/0254035 | A1 | 10/2009 | Kohlbrenner et al. |
| 2009/0292240 | A1 | 11/2009 | Kramer et al. |
| 2009/0299278 | A1 | 12/2009 | Lesch, Jr. et al. |
| 2009/0304812 | A1 | 12/2009 | Stainforth et al. |
| 2009/0312705 | A1 | 12/2009 | Grunhut |
| 2009/0318361 | A1 | 12/2009 | Noera et al. |
| 2010/0016326 | A1 | 1/2010 | Will |
| 2010/0036318 | A1 | 2/2010 | Raday et al. |
| 2010/0049125 | A1 | 2/2010 | James et al. |
| 2010/0069845 | A1 | 3/2010 | Marshall et al. |
| 2010/0076378 | A1 | 3/2010 | Runfola |
| 2010/0076400 | A1 | 3/2010 | Wall |
| 2010/0087847 | A1 | 4/2010 | Hong |
| 2010/0094214 | A1 | 4/2010 | Abry et al. |
| 2010/0094324 | A1 | 4/2010 | Huang et al. |
| 2010/0100039 | A1 | 4/2010 | Wyrick |
| 2010/0114058 | A1 | 5/2010 | Weitzel et al. |
| 2010/0121272 | A1 | 5/2010 | Marshall et al. |
| 2010/0137798 | A1 | 6/2010 | Streit et al. |
| 2010/0152699 | A1 | 6/2010 | Ferrari et al. |
| 2010/0152702 | A1 | 6/2010 | Vigil et al. |
| 2010/0160894 | A1 | 6/2010 | Julian et al. |
| 2010/0168677 | A1 | 7/2010 | Gabriel et al. |
| 2010/0174268 | A1 | 7/2010 | Wilmot et al. |
| 2010/0191217 | A1 | 7/2010 | Hommann et al. |
| 2010/0204678 | A1 | 8/2010 | Imran |
| 2010/0217105 | A1 | 8/2010 | Yodfat et al. |
| 2010/0228193 | A1 | 9/2010 | Wyrick |
| 2010/0249746 | A1 | 9/2010 | Klein |
| 2010/0256570 | A1 | 10/2010 | Maritan |
| 2010/0258631 | A1 | 10/2010 | Rueblinger et al. |
| 2010/0262082 | A1 | 10/2010 | Brooks et al. |
| 2010/0262083 | A1 | 10/2010 | Grunhut et al. |
| 2010/0268170 | A1 | 10/2010 | Carrel et al. |
| 2010/0274198 | A1 | 10/2010 | Bechtold |
| 2010/0274273 | A1 | 10/2010 | Schraga et al. |
| 2010/0288593 | A1 | 11/2010 | Chiesa et al. |
| 2010/0292643 | A1 | 11/2010 | Wilmot et al. |
| 2010/0292653 | A1 | 11/2010 | Maritan |
| 2010/0298780 | A1 | 11/2010 | Laiosa |
| 2010/0312196 | A1 | 12/2010 | Hirschel et al. |
| 2010/0318035 | A1 | 12/2010 | Edwards et al. |
| 2010/0318037 | A1 | 12/2010 | Young et al. |
| 2010/0324480 | A1 | 12/2010 | Chun |
| 2011/0021989 | A1 | 1/2011 | Janek et al. |
| 2011/0034879 | A1 | 2/2011 | Crow |
| 2011/0054414 | A1 | 3/2011 | Shang et al. |
| 2011/0077599 | A1 | 3/2011 | Wozencroft |
| 2011/0087192 | A1 | 4/2011 | Uhland et al. |
| 2011/0098655 | A1 | 4/2011 | Jennings et al. |
| 2011/0098656 | A1 | 4/2011 | Burnell et al. |
| 2011/0125076 | A1 | 5/2011 | Kraft et al. |
| 2011/0125100 | A1 | 5/2011 | Schwirtz et al. |
| 2011/0137246 | A1 | 6/2011 | Cali et al. |
| 2011/0137247 | A1 | 6/2011 | Mesa et al. |
| 2011/0144594 | A1 | 6/2011 | Sund et al. |
| 2011/0190725 | A1 | 8/2011 | Pettis et al. |
| 2011/0196300 | A1 | 8/2011 | Edwards et al. |
| 2011/0196311 | A1 | 8/2011 | Bicknell et al. |
| 2011/0224616 | A1 | 9/2011 | Slate et al. |
| 2011/0224620 | A1 | 9/2011 | Johansen et al. |
| 2011/0238003 | A1 | 9/2011 | Bruno-Raimondi et al. |
| 2011/0269750 | A1 | 11/2011 | Kley et al. |
| 2011/0319864 | A1 | 12/2011 | Beller et al. |
| 2012/0004608 | A1 | 1/2012 | Lesch, Jr. |
| 2012/0016296 | A1 | 1/2012 | Charles |
| 2012/0046609 | A1 | 2/2012 | Mesa et al. |
| 2012/0053563 | A1 | 3/2012 | Du |
| 2012/0059319 | A1 | 3/2012 | Segal |
| 2012/0071829 | A1 | 3/2012 | Edwards et al. |
| 2012/0095443 | A1 | 4/2012 | Ferrari et al. |
| 2012/0101475 | A1 | 4/2012 | Wilmot et al. |
| 2012/0116318 | A1 | 5/2012 | Edwards et al. |
| 2012/0123350 | A1 | 5/2012 | Giambattista et al. |
| 2012/0123385 | A1 | 5/2012 | Edwards et al. |
| 2012/0130318 | A1 | 5/2012 | Young |
| 2012/0130342 | A1 | 5/2012 | Cleathero |
| 2012/0136303 | A1 | 5/2012 | Cleathero |
| 2012/0136318 | A1 | 5/2012 | Lanin et al. |
| 2012/0143144 | A1 | 6/2012 | Young |
| 2012/0157931 | A1 | 6/2012 | Nzike |
| 2012/0157965 | A1 | 6/2012 | Wotton et al. |
| 2012/0172809 | A1 | 7/2012 | Plumptre |
| 2012/0172811 | A1 | 7/2012 | Enggaard et al. |
| 2012/0172812 | A1 | 7/2012 | Plumptre et al. |
| 2012/0172813 | A1 | 7/2012 | Plumptre et al. |
| 2012/0172814 | A1 | 7/2012 | Plumptre et al. |
| 2012/0172815 | A1 | 7/2012 | Holmqvist |
| 2012/0172816 | A1 | 7/2012 | Boyd et al. |
| 2012/0172818 | A1 | 7/2012 | Harms et al. |
| 2012/0172885 | A1 | 7/2012 | Drapeau et al. |
| 2012/0179100 | A1 | 7/2012 | Sadowski et al. |
| 2012/0179137 | A1 | 7/2012 | Bartlett et al. |

(56) References Cited

U.S. PATENT DOCUMENTS

| | | | |
|---|---|---|---|
| 2012/0184900 | A1 | 7/2012 | Marshall et al. |
| 2012/0184917 | A1 | 7/2012 | Bom et al. |
| 2012/0184918 | A1 | 7/2012 | Bostrom |
| 2012/0186075 | A1 | 7/2012 | Edginton |
| 2012/0191048 | A1 | 7/2012 | Eaton |
| 2012/0191049 | A1 | 7/2012 | Harms et al. |
| 2012/0197209 | A1 | 8/2012 | Bicknell et al. |
| 2012/0197213 | A1 | 8/2012 | Kohlbrenner et al. |
| 2012/0203184 | A1 | 8/2012 | Selz et al. |
| 2012/0203185 | A1 | 8/2012 | Kristensen et al. |
| 2012/0203186 | A1 | 8/2012 | Vogt et al. |
| 2012/0209192 | A1 | 8/2012 | Alexandersson |
| 2012/0209200 | A1 | 8/2012 | Jones et al. |
| 2012/0209210 | A1 | 8/2012 | Plumptre et al. |
| 2012/0209211 | A1 | 8/2012 | Plumptre et al. |
| 2012/0209212 | A1 | 8/2012 | Plumptre et al. |
| 2012/0215162 | A1 | 8/2012 | Nielsen et al. |
| 2012/0215176 | A1 | 8/2012 | Veasey et al. |
| 2012/0220929 | A1 | 8/2012 | Nagel et al. |
| 2012/0220941 | A1 | 8/2012 | Jones |
| 2012/0220953 | A1 | 8/2012 | Holmqvist |
| 2012/0220954 | A1 | 8/2012 | Cowe |
| 2012/0226226 | A1 | 9/2012 | Edwards et al. |
| 2012/0230620 | A1 | 9/2012 | Holdgate et al. |
| 2012/0232517 | A1 | 9/2012 | Saiki |
| 2012/0245516 | A1 | 9/2012 | Tschirren et al. |
| 2012/0245532 | A1 | 9/2012 | Frantz et al. |
| 2012/0253274 | A1 | 10/2012 | Karlsson et al. |
| 2012/0253287 | A1 | 10/2012 | Giambattista et al. |
| 2012/0253288 | A1 | 10/2012 | Dasbach et al. |
| 2012/0253289 | A1 | 10/2012 | Cleathero |
| 2012/0253290 | A1 | 10/2012 | Geertsen |
| 2012/0253314 | A1 | 10/2012 | Harish et al. |
| 2012/0259285 | A1 | 10/2012 | Schabbach et al. |
| 2012/0265153 | A1 | 10/2012 | Jugl et al. |
| 2012/0267761 | A1 | 10/2012 | Kim et al. |
| 2012/0271233 | A1 | 10/2012 | Bruggemann et al. |
| 2012/0271243 | A1 | 10/2012 | Plumptre et al. |
| 2012/0277724 | A1 | 11/2012 | Larsen et al. |
| 2012/0283645 | A1 | 11/2012 | Veasey et al. |
| 2012/0283648 | A1 | 11/2012 | Veasey et al. |
| 2012/0283649 | A1 | 11/2012 | Veasey et al. |
| 2012/0283650 | A1 | 11/2012 | MacDonald et al. |
| 2012/0283651 | A1 | 11/2012 | Veasey et al. |
| 2012/0283652 | A1 | 11/2012 | MacDonald et al. |
| 2012/0283654 | A1 | 11/2012 | MacDonald et al. |
| 2012/0283660 | A1 | 11/2012 | Jones et al. |
| 2012/0283661 | A1 | 11/2012 | Jugl et al. |
| 2012/0289907 | A1 | 11/2012 | Veasey et al. |
| 2012/0289908 | A1 | 11/2012 | Kouyoumjian et al. |
| 2012/0289909 | A1 | 11/2012 | Raab et al. |
| 2012/0289929 | A1 | 11/2012 | Boyd et al. |
| 2012/0291778 | A1 | 11/2012 | Nagel et al. |
| 2012/0296276 | A1 | 11/2012 | Nicholls et al. |
| 2012/0296287 | A1 | 11/2012 | Veasey et al. |
| 2012/0302989 | A1 | 11/2012 | Kramer et al. |
| 2012/0302992 | A1 | 11/2012 | Brooks et al. |
| 2012/0310156 | A1 | 12/2012 | Karlsson et al. |
| 2012/0310206 | A1 | 12/2012 | Kouyoumjian et al. |
| 2012/0310208 | A1 | 12/2012 | Kirchhofer |
| 2012/0310289 | A1 | 12/2012 | Bottlang et al. |
| 2012/0316508 | A1 | 12/2012 | Kirchhofer |
| 2012/0323177 | A1 | 12/2012 | Adams et al. |
| 2012/0323186 | A1 | 12/2012 | Karlsen et al. |
| 2012/0325865 | A1 | 12/2012 | Forstreuter et al. |
| 2012/0330228 | A1 | 12/2012 | Day et al. |
| 2013/0006191 | A1 | 1/2013 | Jugl et al. |
| 2013/0006192 | A1 | 1/2013 | Teucher et al. |
| 2013/0006193 | A1 | 1/2013 | Veasey et al. |
| 2013/0006310 | A1 | 1/2013 | Bottlang et al. |
| 2013/0012871 | A1 | 1/2013 | Pommereu |
| 2013/0012884 | A1 | 1/2013 | Pommereu et al. |
| 2013/0012885 | A1 | 1/2013 | Bode et al. |
| 2013/0018310 | A1 | 1/2013 | Boyd et al. |
| 2013/0018313 | A1 | 1/2013 | Kramer et al. |
| 2013/0018317 | A1 | 1/2013 | Bobroff et al. |
| 2013/0018323 | A1 | 1/2013 | Boyd et al. |
| 2013/0018327 | A1 | 1/2013 | Dasbach et al. |
| 2013/0018328 | A1 | 1/2013 | Jugl et al. |
| 2013/0023830 | A1 | 1/2013 | Bode |
| 2013/0030367 | A1 | 1/2013 | Wotton et al. |
| 2013/0030378 | A1 | 1/2013 | Jugl et al. |
| 2013/0030383 | A1 | 1/2013 | Keitel |
| 2013/0030409 | A1 | 1/2013 | Macdonald et al. |
| 2013/0035641 | A1 | 2/2013 | Moller et al. |
| 2013/0035642 | A1 | 2/2013 | Daniel |
| 2013/0035644 | A1 | 2/2013 | Giambattista et al. |
| 2013/0035645 | A1 | 2/2013 | Bicknell et al. |
| 2013/0035647 | A1 | 2/2013 | Veasey et al. |
| 2013/0041321 | A1 | 2/2013 | Cross et al. |
| 2013/0041324 | A1 | 2/2013 | Daniel |
| 2013/0041325 | A1 | 2/2013 | Helmer et al. |
| 2013/0041327 | A1 | 2/2013 | Daniel |
| 2013/0041328 | A1 | 2/2013 | Daniel |
| 2013/0041347 | A1 | 2/2013 | Daniel |
| 2013/0060231 | A1 | 3/2013 | Adlon et al. |

FOREIGN PATENT DOCUMENTS

| | | |
|---|---|---|
| AU | 2007253481 | 11/2007 |
| AU | 2008231897 | 10/2008 |
| AU | 2008309660 | 4/2009 |
| AU | 2009272992 | 1/2010 |
| AU | 2009299888 | 4/2010 |
| AU | 2009326322 | 8/2011 |
| AU | 2009341040 | 9/2011 |
| AU | 2010239762 | 12/2011 |
| AU | 2010242096 | 12/2011 |
| AU | 2010254627 | 1/2012 |
| AU | 2010260568 | 2/2012 |
| AU | 2010260569 | 2/2012 |
| AU | 2010303987 | 5/2012 |
| AU | 2010332857 | 7/2012 |
| AU | 2010332862 | 7/2012 |
| AU | 2010337136 | 7/2012 |
| AU | 2010338469 | 7/2012 |
| AU | 2011214922 | 8/2012 |
| AU | 2011221472 | 8/2012 |
| AU | 2011231688 | 9/2012 |
| AU | 2011231691 | 9/2012 |
| AU | 2011224884 | 10/2012 |
| AU | 2011231570 | 10/2012 |
| AU | 2011231697 | 10/2012 |
| AU | 2011233733 | 10/2012 |
| AU | 2011234479 | 10/2012 |
| AU | 2011238967 | 11/2012 |
| AU | 2011244232 | 11/2012 |
| AU | 2011244236 | 11/2012 |
| AU | 2011244237 | 11/2012 |
| AU | 2011249098 | 11/2012 |
| AU | 2011262408 | 12/2012 |
| AU | 2011273721 | 1/2013 |
| AU | 2011273722 | 1/2013 |
| AU | 2011273723 | 1/2013 |
| AU | 2011273724 | 1/2013 |
| AU | 2011273725 | 1/2013 |
| AU | 2011273726 | 1/2013 |
| AU | 2011273727 | 1/2013 |
| AU | 2011273728 | 1/2013 |
| BR | 0208013 | 3/2004 |
| BR | 0308262 | 1/2005 |
| BR | PI712805 | 10/2012 |
| BR | PI0713802-4 | 11/2012 |
| BR | 0214721 | 12/2012 |
| CA | 2552177 | 7/1999 |
| CA | 2689022 | 11/2002 |
| CA | 02702412 | 12/2008 |
| CN | 101094700 | 12/2007 |
| CN | 101128231 | 2/2008 |
| CN | 101400394 | 4/2009 |
| CN | 101479000 | 7/2009 |
| CN | 101516421 | 8/2009 |
| CN | 101557849 | 10/2009 |
| CN | 101563124 | 10/2009 |

(56) References Cited

FOREIGN PATENT DOCUMENTS

| | | |
|---|---|---|
| CN | 101600468 | 12/2009 |
| CN | 101610804 | 12/2009 |
| CN | 101678172 | 3/2010 |
| CN | 101687078 | 3/2010 |
| CN | 101687079 | 3/2010 |
| CN | 101909673 | 12/2010 |
| CN | 101912650 | 12/2010 |
| CN | 101939036 | 1/2011 |
| CN | 102548599 | 7/2012 |
| CN | 102548601 | 7/2012 |
| CN | 102548602 | 7/2012 |
| CN | 102573955 | 7/2012 |
| CN | 102573958 | 7/2012 |
| CN | 102573960 | 7/2012 |
| CN | 102573963 | 7/2012 |
| CN | 10263017 4 | 8/2012 |
| CN | 102630172 | 8/2012 |
| CN | 102630173 | 8/2012 |
| CN | 102639170 | 8/2012 |
| CN | 102639171 | 8/2012 |
| CN | 102655899 | 9/2012 |
| CN | 102665800 | 9/2012 |
| CN | 102665802 | 9/2012 |
| CN | 102686255 | 9/2012 |
| CN | 102686256 | 9/2012 |
| CN | 102686258 | 9/2012 |
| CN | 102727965 | 10/2012 |
| CN | 102740907 | 10/2012 |
| CN | 102753222 | 10/2012 |
| CN | 102753223 | 10/2012 |
| CN | 102753224 | 10/2012 |
| CN | 102753227 | 10/2012 |
| CN | 102770170 | 11/2012 |
| CN | 102770173 | 11/2012 |
| CN | 102781499 | 11/2012 |
| CN | 102781500 | 11/2012 |
| CN | 102802699 | 11/2012 |
| CN | 102802702 | 11/2012 |
| CN | 102802703 | 11/2012 |
| CN | 102665801 | 12/2012 |
| CN | 102821801 | 12/2012 |
| CN | 102821802 | 12/2012 |
| CN | 102821805 | 12/2012 |
| CN | 102834133 | 12/2012 |
| CN | 102869399 | 1/2013 |
| DE | 102006041809 | 3/2008 |
| DE | 202011110155 | 12/2012 |
| DK | 1646844 | 12/2009 |
| DK | 2229201 | 7/2012 |
| DK | 2274032 | 10/2012 |
| DK | 02346552 | 11/2012 |
| DK | 2288400 | 1/2013 |
| DK | 2373361 | 1/2013 |
| EG | B25844 | 9/2012 |
| EP | 0072057 | 2/1983 |
| EP | 0103664 | 3/1984 |
| EP | 1752174 | 3/1986 |
| EP | 245895 | 11/1987 |
| EP | 255044 | 2/1988 |
| EP | 361668 | 4/1990 |
| EP | 0518416 | 12/1992 |
| EP | 525525 | 2/1993 |
| EP | 1161961 | 12/2001 |
| EP | 1307012 | 5/2003 |
| EP | 1518575 | 3/2005 |
| EP | 1140260 | 8/2005 |
| EP | 2174682 | 4/2010 |
| EP | 2258424 | 12/2010 |
| EP | 2258425 | 12/2010 |
| EP | 02275158 | 1/2011 |
| EP | 2364742 | 9/2011 |
| EP | 2393062 | 12/2011 |
| EP | 2471564 | 7/2012 |
| EP | 02477681 | 7/2012 |
| EP | 02484395 | 8/2012 |
| EP | 2526987 | 11/2012 |
| EP | 02529773 | 12/2012 |
| EP | 02529774 | 12/2012 |
| EP | 02529775 | 12/2012 |
| EP | 2549789 | 1/2013 |
| ES | 02385630 | 7/2012 |
| ES | 2389866 | 11/2012 |
| ES | 2392667 | 12/2012 |
| ES | 02393173 | 12/2012 |
| FR | 2506161 | 11/1982 |
| FR | 2635009 | 2/1990 |
| GB | 6677523 | 8/1952 |
| GB | 1181037 | 2/1970 |
| GB | 1216813 | 12/1970 |
| GB | 2463034 | 3/2010 |
| IL | 171247 | 8/2012 |
| IL | 198750 | 10/2012 |
| JP | 10-507935 | 8/1998 |
| JP | 11-347121 | 12/1999 |
| JP | 2000-245839 | 9/2000 |
| JP | 2001-523485 | 11/2001 |
| JP | 5016490 | 5/2008 |
| JP | 5026411 | 11/2008 |
| JP | 5033792 | 11/2008 |
| JP | 5074397 | 2/2009 |
| JP | 2009-529395 | 8/2009 |
| JP | 5066177 | 9/2009 |
| JP | 5039135 | 11/2009 |
| JP | 5044625 | 12/2009 |
| JP | 2010-005414 | 1/2010 |
| JP | 2010-046507 | 3/2010 |
| JP | 4990151 | 8/2012 |
| JP | 4992147 | 8/2012 |
| JP | 4994370 | 8/2012 |
| JP | 5001001 | 8/2012 |
| JP | 2012143646 | 8/2012 |
| JP | 2012148198 | 8/2012 |
| JP | 2012176295 | 9/2012 |
| JP | 2012183322 | 9/2012 |
| JP | 2012520128 | 9/2012 |
| JP | 2012521821 | 9/2012 |
| JP | 2012521825 | 9/2012 |
| JP | 2012521826 | 9/2012 |
| JP | 2012521827 | 9/2012 |
| JP | 2012521828 | 9/2012 |
| JP | 2012521829 | 9/2012 |
| JP | 2012521830 | 9/2012 |
| JP | 2012521831 | 9/2012 |
| JP | 2012521834 | 9/2012 |
| JP | 2012522547 | 9/2012 |
| JP | 2012-525172 | 10/2012 |
| JP | 2012-525180 | 10/2012 |
| JP | 2012523876 | 10/2012 |
| JP | 2012525185 | 10/2012 |
| JP | 2012525200 | 10/2012 |
| JP | 5084825 | 11/2012 |
| JP | 2012232151 | 11/2012 |
| JP | 2012528618 | 11/2012 |
| JP | 2012528619 | 11/2012 |
| JP | 2012528620 | 11/2012 |
| JP | 2012528621 | 11/2012 |
| JP | 2012528622 | 11/2012 |
| JP | 2012528623 | 11/2012 |
| JP | 2012528624 | 11/2012 |
| JP | 2012528625 | 11/2012 |
| JP | 2012528626 | 11/2012 |
| JP | 2012528627 | 11/2012 |
| JP | 2012528628 | 11/2012 |
| JP | 2012528629 | 11/2012 |
| JP | 2012528630 | 11/2012 |
| JP | 2012528631 | 11/2012 |
| JP | 2012528632 | 11/2012 |
| JP | 2012528633 | 11/2012 |
| JP | 2012528634 | 11/2012 |
| JP | 2012528635 | 11/2012 |
| JP | 2012528636 | 11/2012 |
| JP | 2012528637 | 11/2012 |
| JP | 2012528638 | 11/2012 |
| JP | 2012528640 | 11/2012 |

(56) References Cited

FOREIGN PATENT DOCUMENTS

| | | |
|---|---|---|
| JP | 2012530576 | 12/2012 |
| JP | 2012532635 | 12/2012 |
| JP | 2012532636 | 12/2012 |
| JP | 2012532717 | 12/2012 |
| JP | 2012532720 | 12/2012 |
| JP | 2012532721 | 12/2012 |
| JP | 2012532722 | 12/2012 |
| JP | 5112330 | 1/2013 |
| JP | 5113847 | 1/2013 |
| KR | 101160735 | 7/2012 |
| KR | 20120099022 | 9/2012 |
| KR | 20120099101 | 9/2012 |
| KR | 20120102597 | 9/2012 |
| KR | 20120106754 | 9/2012 |
| KR | 20120106756 | 9/2012 |
| KR | 20120112503 | 10/2012 |
| NO | 332622 | 10/2003 |
| NZ | 572765 | 8/2012 |
| NZ | 587235 | 8/2012 |
| NZ | 00590352 | 10/2012 |
| PL | 2023982 | 11/2012 |
| PT | 2274032 | 10/2012 |
| PT | 2346552 | 11/2012 |
| RU | 2462275 | 3/2011 |
| RU | 2459247 | 8/2012 |
| RU | 2011104496 | 8/2012 |
| RU | 2460546 | 9/2012 |
| RU | 2011109925 | 10/2012 |
| RU | 2011119019 | 11/2012 |
| SG | 181710 | 7/2012 |
| SG | 181790 | 7/2012 |
| SG | 184182 | 10/2012 |
| SG | 184328 | 11/2012 |
| SG | 184500 | 11/2012 |
| SG | 184501 | 11/2012 |
| SG | 184502 | 11/2012 |
| SI | 2274032 | 12/2012 |
| SI | 2346552 | 12/2012 |
| WO | WO 1988/008724 | 11/1988 |
| WO | WO 1991/013299 | 9/1991 |
| WO | WO 1991/013430 | 9/1991 |
| WO | WO 1992/019296 | 11/1992 |
| WO | WO 1994/009839 | 5/1994 |
| WO | WO 1994/011041 | 5/1994 |
| WO | WO 95/29720 | 11/1995 |
| WO | WO 1995/029730 | 11/1995 |
| WO | WO 1996/021482 | 7/1996 |
| WO | WO 1997/014455 | 4/1997 |
| WO | WO 1997/021457 | 6/1997 |
| WO | WO 1997/41907 | 11/1997 |
| WO | WO 1998/031369 | 7/1998 |
| WO | WO 1998/032451 | 7/1998 |
| WO | WO 1997 /048430 | 12/1998 |
| WO | WO 1999/003521 | 1/1999 |
| WO | WO 1999/010030 | 3/1999 |
| WO | WO 1999/022789 | 5/1999 |
| WO | WO 1999/022790 | 5/1999 |
| WO | WO 1999/062525 | 12/1999 |
| WO | WO 2000/006228 | 2/2000 |
| WO | WO 2000/024441 | 5/2000 |
| WO | WO 2000/029050 | 5/2000 |
| WO | WO 2001/93926 | 12/2001 |
| WO | WO 2002/083216 | 10/2002 |
| WO | WO 2002/089805 | 11/2002 |
| WO | WO 2003/047663 | 6/2003 |
| WO | WO 2003/068290 | 8/2003 |
| WO | WO 2003/070296 | 8/2003 |
| WO | WO 03070296 | 8/2003 |
| WO | WO 2003/097133 | 11/2003 |
| WO | WO 2003/3097133 | 11/2003 |
| WO | WO 2004/028598 | 4/2004 |
| WO | WO 2004/041331 | 5/2004 |
| WO | WO 2004/047892 | 6/2004 |
| WO | WO 2004/108194 | 12/2004 |
| WO | WO 2005/002653 | 1/2005 |
| WO | WO 2005/005929 | 1/2005 |
| WO | WO 2005/009515 | 2/2005 |
| WO | WO 2005/053778 | 6/2005 |
| WO | WO 2006/086899 | 8/2006 |
| WO | WO 2006/130098 | 12/2006 |
| WO | WO 2007/047200 | 4/2007 |
| WO | WO 2007 /063342 | 6/2007 |
| WO | WO 2007/100899 | 9/2007 |
| WO | WO 2006/079064 | 11/2007 |
| WO | WO 2007/129106 | 11/2007 |
| WO | WO 2007/131013 | 11/2007 |
| WO | WO 2007/131025 | 11/2007 |
| WO | WO 2007/143676 | 12/2007 |
| WO | WO 2008/005315 | 1/2008 |
| WO | WO 2008/009476 | 1/2008 |
| WO | WO 2008/058666 | 5/2008 |
| WO | WO 2008/089886 | 7/2008 |
| WO | WO 2008/100576 | 8/2008 |
| WO | WO 2008/107378 | 9/2008 |
| WO | WO 2008/112472 | 9/2008 |
| WO | WO 2007/104636 | 12/2008 |
| WO | WO 2009/049885 | 4/2009 |
| WO | WO 2008/071804 | 8/2009 |
| WO | WO 2009/114542 | 9/2009 |
| WO | WO 2009/132778 | 11/2009 |
| WO | WO 2009/141005 | 11/2009 |
| WO | WO 2010/003569 | 1/2010 |
| WO | WO 2010/043533 | 4/2010 |
| WO | WO 2010/046394 | 4/2010 |
| WO | WO 2010/097116 | 9/2010 |
| WO | WO 2010/108116 | 9/2010 |
| WO | WO 2011/023736 | 3/2011 |
| WO | WO 2011/023882 | 3/2011 |
| WO | WO 2011/035877 | 3/2011 |
| WO | WO 2011/036133 | 3/2011 |
| WO | WO 2011/036134 | 3/2011 |
| WO | WO 2011/039163 | 4/2011 |
| WO | WO 2011/039201 | 4/2011 |
| WO | WO 2011/039202 | 4/2011 |
| WO | WO 2011/039207 | 4/2011 |
| WO | WO 2011/039208 | 4/2011 |
| WO | WO 2011/039209 | 4/2011 |
| WO | WO 2011/039211 | 4/2011 |
| WO | WO 2011/039216 | 4/2011 |
| WO | WO 2011/039217 | 4/2011 |
| WO | WO 2011/039218 | 4/2011 |
| WO | WO 2011/039219 | 4/2011 |
| WO | WO 2011/039228 | 4/2011 |
| WO | WO 2011/039231 | 4/2011 |
| WO | WO 2011/039232 | 4/2011 |
| WO | WO 2011/039233 | 4/2011 |
| WO | WO 2011/039236 | 4/2011 |
| WO | WO 2011/040861 | 4/2011 |
| WO | WO 2011/042537 | 4/2011 |
| WO | WO 2011/042540 | 4/2011 |
| WO | WO 2011/043714 | 4/2011 |
| WO | WO 2011/054775 | 5/2011 |
| WO | WO 2011/056127 | 5/2011 |
| WO | WO 2011/060087 | 5/2011 |
| WO | WO 2011/067615 | 6/2011 |
| WO | WO 2011/069936 | 6/2011 |
| WO | WO 2011/073302 | 6/2011 |
| WO | WO 2011/073307 | 6/2011 |
| WO | WO 2011/076280 | 6/2011 |
| WO | WO 2011/080092 | 7/2011 |
| WO | WO 2011/081867 | 7/2011 |
| WO | WO 2011/081885 | 7/2011 |
| WO | WO 2011/089206 | 7/2011 |
| WO | WO 2011/089207 | 7/2011 |
| WO | WO 2011/095478 | 8/2011 |
| WO | WO 2011/095480 | 8/2011 |
| WO | WO 2011/095483 | 8/2011 |
| WO | WO 2011/095486 | 8/2011 |
| WO | WO 2011/095488 | 8/2011 |
| WO | WO 2011/095489 | 8/2011 |
| WO | WO 2011/095503 | 8/2011 |
| WO | WO 2011/099918 | 8/2011 |
| WO | WO 2011/101349 | 8/2011 |
| WO | WO 2011/101351 | 8/2011 |

(56) References Cited

FOREIGN PATENT DOCUMENTS

| | | |
|---|---|---|
| WO | WO 2011/101375 | 8/2011 |
| WO | WO 2011/101376 | 8/2011 |
| WO | WO 2011/101377 | 8/2011 |
| WO | WO 2011/101378 | 8/2011 |
| WO | WO 2011/101379 | 8/2011 |
| WO | WO 2011/101380 | 8/2011 |
| WO | WO 2011/101381 | 8/2011 |
| WO | WO 2011/101382 | 8/2011 |
| WO | WO 2011/101383 | 8/2011 |
| WO | WO 2011/107805 | 9/2011 |
| WO | WO 2011/109205 | 9/2011 |
| WO | WO 2011/110464 | 9/2011 |
| WO | WO 2011/110465 | 9/2011 |
| WO | WO 2011/110466 | 9/2011 |
| WO | WO 2011/111006 | 9/2011 |
| WO | WO 2011/112136 | 9/2011 |
| WO | WO 2011/113806 | 9/2011 |
| WO | WO 2011/117212 | 9/2011 |
| WO | WO 2011/117284 | 9/2011 |
| WO | WO 2012020084 | 2/2012 |
| WO | WO 2012022771 | 2/2012 |
| WO | WO 2012/090186 | 7/2012 |
| WO | WO 2012/122643 | 9/2012 |

OTHER PUBLICATIONS

Becks et al., "Comparison of Conventional Twice-Daily Subcutaneous Needle Injections to Multiple Jet Injections of Insulin in Insulin-Dependent Diabetes", Clinical and Investigative Medicine, 1981, p. 33B.
Binder, "Absorption of Injected Insulin", ACTA Pharmacological ET Toxicologica, 1969, 27(Supp 2), 3 pages.
Bonetti et al., "An Extended-Release formulation of Methotrexate for Subcutaneous Administration", Cancer Chemotherapy Pharmacology, 1994, 33, 303-306.
Braun et al., "Comparison of the Clinical Efficacy and Safety of Subcutaneous Versus Oral Administration of Methotrexate in Patients with Active Rheumatoid Arthritis", Arthritis and Rheumatism, Jan. 2008, 58(1 ), pp. 73-81.
Chen et al., "Blood Lipid Profiles and Peripheral Blood Mononuclear Cell Cholesterol Metabolism Gene Expression in Patients with and Without Methotrexate" BMC Medicine, 2011, 9(4), 9 pages.
Chiasson et al., "Continuous Subcutaneous Insulin Infusion (Mill-Hill Infuser) Versus Multiple Injections (Medi-Jector) in the Treatment of Insulin-Dependent Diabetes Mellitus and the Effects of Metabolic Control on Microangiopathy" Diabetes Care, Jul.-Aug. 1984, 7(4), pp. 331-337.
Cohn et al., "Clincal Experience with Jet Insulin Injection in Diabetes Mellitus Therapy: A Clue to the Pathogenesis of Lipodystrophy", Ala. J. Med. Sci., 1974, 11(3), pp. 265-272.
Cowie et al., "Physical and Metabolic Characteristics of Persons with Diabetes", National Institutes of Health/National Institute of Diabetes and Digestive and Kidney Diseases, 1995, 95(1468), pp. 117-120.
European Patent Application No. 03707823.5, Supplementary European Search Report, dated Mar. 30, 2005 with Communication dated Apr. 25, 2005 regarding Proceeding Further with the European Patent Application Pursuant to Article 96(1), and Rule 51(1) EPC, 3 pages.
European Patent Application No. 00976612.2, Communication Pursuant to Article 96(2) EPC, dated May 10, 2004, 5 pages.
Hingson et al., "A Survey of the Development of Jet Injection in Parenteral Therapy", Nov./Dec. 1952, 31 (6), pp. 361-366.
Hoekstra et al., Bioavailability of Higher Dose Methotrexate Comparing Oral and Subcutaneous Administration i n Patients with Rheumatoid Arthritis, The Journal of Rheumatology, 2004, 31 (4), pp. 645-648.
International Patent Application No. PCT/US2012/46742, International Search Report and Written Opinion dated Nov. 16, 2012, 11 pages.
International Patent Application No. PCT/US2009/052835, International Search Report dated Mar. 15, 2010, 5 pages.
International Patent Application No. PCT/US2013/029085, International Search Report dated May 13, 2013, 2 pages.
International Patent Application No. PCT/US2010/028011, International Search Report, dated Jun. 29, 2010, 5 pages.
International Patent Application No. PCT/US2009/036682, International Search Report, dated Jul. 7, 2009, 5 pages.
International Patent Application No. PCT/US2007/068010, International Search Report, dated Sep. 24, 2007, 3 pages.
International Patent Application No. PCT/US03/03917, International Search Report, dated Nov. 26, 2003, 1 page.
Jansen et al., Methotrexaat Buiten de Kliniek, Pharmaceutisch Weekblad, Nov. 1999, 134(46), pp. 1592-1596.
Japanese Patent Application No. 2007-552367, Office Action dated Apr. 9, 2011.
Katoulis et al., Efficacy of a New Needleless Insulin Delivery System Monitoring of Blood Glucose Fluctuations and Free Insulin Levels, The International Journal of Artificial Organs, 1989, 12(5), 333-339.
Kurnik et al., "Bioavailability of Oral vs. Subcutaneous low-dose Methotrexate in Patients with Crohn's Disease", Aliment Pharmacol Ther., Apr. 2003, 18, pp. 57-63.
Malone et al., "Comparison of Insulin Levels After Injection by Jet Stream and Disposable Insulin Syringe", Diabetes Care, Nov.-Dec. 1986, 9(6), 637-640.
"The Historical Development of Jet Injection and Envisioned Uses in Mass Immunization and Mass Therapy Based Upon Two Decades' Experience", Military Medicine, Jun. 1963, 128, pp. 516-524.
Pehling et al., "Comparison of Plasma Insulin Profiles After Subcutaneous Administration of Insulin by Jet Spray and Conventional Needle Injection in Patients with Insulin-Dependent Diabetes Mellitus", Mayo Clin. Proc., Nov. 1984, 59, pp. 751-754.
Reiss et al., "Atheroprotective Effects of Methotrexate on Reverse Cholesterol Transport Proteins and Foam Cell Transformation in Human THP-1 Monocyte/Macrophages", Arthritis and Rheumatism, Dec. 2008, 58(12), pp. 3675-3683.
Taylor et al., "Plasma Free Insulin Profiles After Administration of Insulin by Jet and Conventional Syringe Injection", Diabetes Care, May-Jun. 1981, 4(3), 337-339.
Weller et al., "Jet Injection of Insulin vs the Syringe-and-Needle Method", JAMA, Mar. 1966, 195(10), pp. 844-847.
Westlake et al., "The Effect of Methotrexate on Cardiovascular Disease in Patients with Rheumatoid Arthritis: A Systematic Literature Review", Rheumatology, Nov. 2009, 49, pp. 295-307.
Worth, "Jet Injection of Insulin: Comparison with Conventional Injection by Syringe and Needle", British Medical Journal, Sep. 1980, 281, pp. 713-714.
International Patent Application No. PCT/US2013/029085, Written Opinion, dated May 13, 2013, 5 pages.
International Patent Application No. PCT/US2010/028011, Written Opinion, dated Jun. 29, 2010, 5 pages.
Zachheim et al., "Subcutaneous Administration of Methotrexate", Journal of the American Academy of Dermatology, 1992, 26(6), p. 1008.
Halle et al., "Twice-Daily Mixed Regular and NPH Insulin Injections with New Jet Injector Versus Conventional Syringes: Pharmacokinetics of Insulin Absorption", Diabetes Care, May-Jun. 1986 9(3), pp. 279-282.
International Patent Application No. PCT/US2012/046639, International Search Report and Written Opinion dated Apr. 22, 2013, 8 pages.
Glynn-Barnhart et al., "Pharmacotherapy: The Journal of Human Pharmacology and Drug Therapy", 1992, 12(5), abstract only, 2 pages.
Hamilton et al., "Why Intramuscular Methotrexate May be More Efficacious Than Oral Dosing in Patients with Rheumatoid Arthritis", British Journal of Rheumatology, 1997, 36(1 ), pp. 86-90.
Stamp et al., "Effects of Changing from Oral to Subcutaneous Methotrexate on Red Blood Cell Methotrexate Polyglutamate Concentrations and Disease Activity in Patients with Rheumatoid Arthritis", The Journal of Rheumatology, 2011, 38(12), 2540-2547.

(56) References Cited

OTHER PUBLICATIONS

Tukova et al., "Methotrexate Bioavailability after Oral and Subcutaneous Administration in Children with Juvenile Idiopathic Arthritis", Clinical and Experimental Rheumatology, 2009, 27, 1047-1053.

Wright et al., "Stability of Methotrexate Injection in Prefilled Plastic Disposable Syringes", International Journal of Pharmaceutics, Aug. 1988, 45(3), 237-244.

Lunenfeld, "Stable Testosterone Levels Achieved with Subcutaneous Testosterone Injections", The aging Male, Mar. 2006, 9(1), 70 pages.

International Patent Application No. PCT/US13/39983, International Search Report, dated Jul. 25, 2013, 3 pages.

International Patent Application No. PCT/US14/23883, International Search Report, dated Jul. 10, 2014, 3 pages.

International Patent Application No. PCT/US 14123485, International Search Report, dated Jul. 7, 2014, 2 pages.

International Patent Application No. PCT/US14/24530, International Search Report, dated Jul. 15, 2014, 2 pages.

International Patent Application No. PCT/US 14124543, International Search Report, dated Jul. 28, 2014, 2 page.

* cited by examiner 1044
312
302a
310
1040

NEEDLE ASSISTED INJECTION DEVICE HAVING REDUCED TRIGGER FORCE

CROSS-REFERENCE TO RELATED APPLICATIONS

This application is a continuation of U.S. patent application Ser. No. 18/927,653, filed 25 Oct. 2024, which is a continuation of U.S. patent application Ser. No. 17/819,171, filed 11 Aug. 2022, now U.S. Pat. No. 12,220,560, which is a continuation of U.S. patent application Ser. No. 16/436,377, filed 10 Jun. 2019, now U.S. Pat. No. 11,446,440, which is a continuation of U.S. patent application Ser. No. 15/155,804, filed 16 May 2016, now U.S. Pat. No. 10,357,609, which in turn is a continuation of U.S. patent application Ser. No. 13/889,190, filed 7 May 2013, now U.S. Pat. No. 9,364,611, which claims benefit from U.S. Provisional Patent Application No. 61/643,659, filed 7 May 2012, U.S. Provisional Patent Application No. 61/643,845, filed 7 May 2012, U.S. Provisional Patent Application No. 61/776,283, filed 11 Mar. 2013, and U.S. Provisional Patent Application No. 61/763,395, filed 11 Feb. 2013, each of which is incorporated herein by reference in its entirety.

FIELD OF THE DISCLOSURE

The present disclosure relates to injection devices, and in particular to a needle assisted jet injector for special medicaments such as testosterone or midazolam.

BACKGROUND INFORMATION

Various injection devices exist that employ an automated mechanism to actuate injection of a liquid medicament into a patient. Examples of such devices include jet injectors (both needle-free and needle-assisted) and traditional, low-pressure auto-injectors (that provide, for example, mechanized delivery of a traditional, finger-powered hypodermic syringe injection). Although the precise mechanisms used to complete an injection can vary, most include a feature that stores kinetic energy that can be used to drive an injection mechanism during use. Further, many injectors include a trigger mechanism configured to ensure that the kinetic energy remains stored until an injection is desired, whereby actuation of the trigger releases the injection mechanism, allowing the stored kinetic energy to drive the injection mechanism to cause injection.

Examples of needle-free jet injectors are described, for example, in U.S. Pat. Nos. 5,599,302 and 4,790,824. These high force injectors are button activated and administer medication as a fine, high velocity jet delivered under sufficient pressure to enable the jet to pass through the skin. The injection mechanism in such needle-free jet injectors can apply a force to a medicament storing chamber within the device such that the pressure required to inject the medicament is created within the chamber.

Traditional self-injectors or auto-injectors like the ones described, for example, in U.S. Pat. Nos. 4,553,962 and 4,378,015 and PCT Publications WO/9929720 and WO/9714455 inject medicament at a rate and in a manner similar to hand-operated hypodermic syringes. The described self-injectors or auto-injectors have needles that are extended at the time of activation to penetrate the user's skin to deliver medicament through movement of the drug container and related needle. Thus, the mechanism that provides the force to deliver the medicament in traditional, low-pressure self-injectors and auto-injectors can also be used to extend the needle and displace the drug container to cause the insertion of the needle through the user's skin and to apply a force to a plunger movably disposed within the drug container to cause the medicament to be expelled from the container through the needle. The auto-injectors manufactured, for example by Owen Mumford, thus use very low pressures to inject the medicament, which is typically injected through a needle in a relatively slow stream. Another self-injector includes the Simponi injector, which includes a window in the housing through which a yellow ram is visible inside a clear medicament container once the injector has been used.

Additionally, needle-assisted jet injectors have also been with higher injection forces that utilize a needle to initially penetrate the skin allowing but not restricted to an insertion depth less than that of a traditional hypodermic injector or low-pressure auto-injectors. Once the skin is penetrated with the needle, a jet mechanism is activated, causing the medicament containing liquid within the injector to be pressurized and expelled through the needle and into the skin. The injection mechanism in needle-assisted jet injectors can be configured to move the drug container and the needle forward to penetrate the skin and exert the necessary injection force to a plunger moveably disposed within the container. Alternatively, the needle and drug container can be positioned to penetrate the skin while keeping the needle and drug container in a stationary position, and the injection mechanism can be structured to pressurize the container. The pressure applied to the medicament within the injector can be less than that of a traditional jet injector, because the outer layers of the skin have already been penetrated by the needle. Similarly, the pressure applied to the medicament is preferably higher than that of a traditional auto-injector or the like, causing the medicament to penetrate the skin and be dispersed into the tissue or injected in the tissue below the skin to a depth that is sufficient so that the medicament remains substantially within the body. An additional benefit of the higher pressure includes a faster time of injection resulting in less psychological trauma to the patient and a decreased likelihood of the user inadvertently terminating the injection prematurely by removing the injector from the injection site.

Because of the stored energy associated with the trigger and injection mechanisms, accidental firing can occur due to sudden movements during shipping or due to mishandling of the device by a user including accidental actuation of the trigger mechanism. Accidental firing of the injection mechanism can cause the medicament to be expelled from the device, which can be at a dangerously high pressure, depending on the type of injection device. Further, accidental firing can cause an injection needle to move forward with respect to the device with sufficient force to penetrate the skin.

Additionally, the dimensions of many components incorporated in injectors typically constrain the design of many injectors. For example, many injectors utilize front firing-initiation mechanisms that typically require an axial translation and engagement with a triggering structure located at the back of the injector. However, this configuration typically promotes binding of the communicating triggering components due to but not limited friction between components in slidable communication and component distortion, which can be advantageous for, e.g., reducing the size of the injection device, being able to view the drug container within the device, etc.

SUMMARY

In one embodiment of the invention, the invention relates to an injector. The injector may include a trigger mechanism including a floating trigger member having a retaining portion, and a ram assembly having a ram configured to pressurize a medicament container for expelling a medicament therefrom, the ram assembly further having a floating trigger engagement member configured to engage the retaining portion of the floating trigger member when the floating trigger member is in a pre-firing condition; an energy source associated with the ram for powering the ram to expel the medicament; and a user-operable firing-initiation member operable for causing an axial rotation of the floating trigger member from the pre-firing condition to a firing condition in which the floating trigger engagement member is released from the retaining portion to allow the energy source to fire the ram.

In one embodiment, the invention further includes an injector housing, wherein the firing initiation member includes a skin-contacting member disposed at a distal end of the injector that is movable proximally with respect to the housing when a force is applied to the skin-contacting member at the distal end of the injector, the firing initiation member being associated with the floating trigger member and configured to cause the axial rotation of the floating trigger member from the pre-firing condition to the firing condition upon a proximal movement of the skin-contacting member with respect to housing.

In another embodiment, the skin-contacting member includes a needle guard that is retractable and is configured to expose a needle connected to the medicament container upon the proximal movement of the skin-contacting member.

In certain embodiments, the needle is in fluid communication with the medicament container for injecting the medicament expelled therefrom during the firing.

In one embodiment, the energy source and the needle are configured for jet injecting the medicament through the needle. In certain embodiments, the energy source is configured to pressurize the medicament to between about 90 p.s.i. and about 500 p.s.i. to jet inject the medicament. In other embodiments, the energy source and needle are configured for injecting the medicament at an average velocity of at least about 1,000 cm/sec within the needle.

In one embodiment, the skin-contacting member includes a first cam, and the floating trigger member includes a second cam, the first cam being operatively associated with the second cam so as to cause axial rotation of the floating trigger member from the pre-firing condition to the firing condition upon proximal movement of the skin-contacting member with respect to the housing.

In certain embodiments, the invention further includes an end cap, the end cap including a ram holding member that axially retains the ram assembly in a proximal position against action of the energy source in the pre-firing position, the retaining portion retaining the floating trigger engagement member engaged and held against firing by the ram holding member.

In one embodiment, the ram is disengaged from the retaining portion, and the energy source overcomes an engagement between the floating trigger engagement member and the ram holding member.

In certain embodiments, the ram assembly is of unitary construction.

In another embodiment, the ram holding member includes a projection that includes a bulge and a groove engaged with the floating trigger engagement member, and the retaining portion retains the engagement of the floating trigger engagement member with the bulge and groove in the pre-firing condition.

In certain embodiments, the invention further includes a container support that is configured for holding the medicament container during injection, and wherein the ram assembly is configured to engage the container support to lock-out the injector after an injection.

In one embodiment, the proximal movement of the user-operable firing-initiation member is blocked by the ram assembly when the injector is locked-out.

In one embodiment, a pre-firing color gamut is visible from the exterior of the injector in the pre-firing condition, the injector further including a housing including a window; and an indicator having an indicator color that is absent from the pre-firing color gamut, which color is hidden from view within the housing in the pre-fired condition, wherein in the fired condition, the indicator color is visible through the window from an exterior of the injector for indicating the fired condition. In certain embodiments, the ram assembly includes the indicator. In other embodiments, the ram assembly entirely occludes the window in the fired condition.

In one embodiment, the medicament includes an androgen. In certain embodiments, the androgen may include testosterone or a derivative or ester thereof. In other embodiments, the androgen includes testosterone cypionate. In another embodiment, the androgen includes testosterone enanthate.

Further, in one embodiment, the medicament includes a compound for the treatment of seizures. In one embodiment, the medicament includes a benzodiazepine. In one embodiment, the benzodiazepine includes midazolam.

BRIEF DESCRIPTION OF THE DRAWINGS

These and other objects, features and advantages of the invention will be apparent from a consideration of the following non-limiting detailed description considered in conjunction with the drawing figures, in which.

Figure 1:
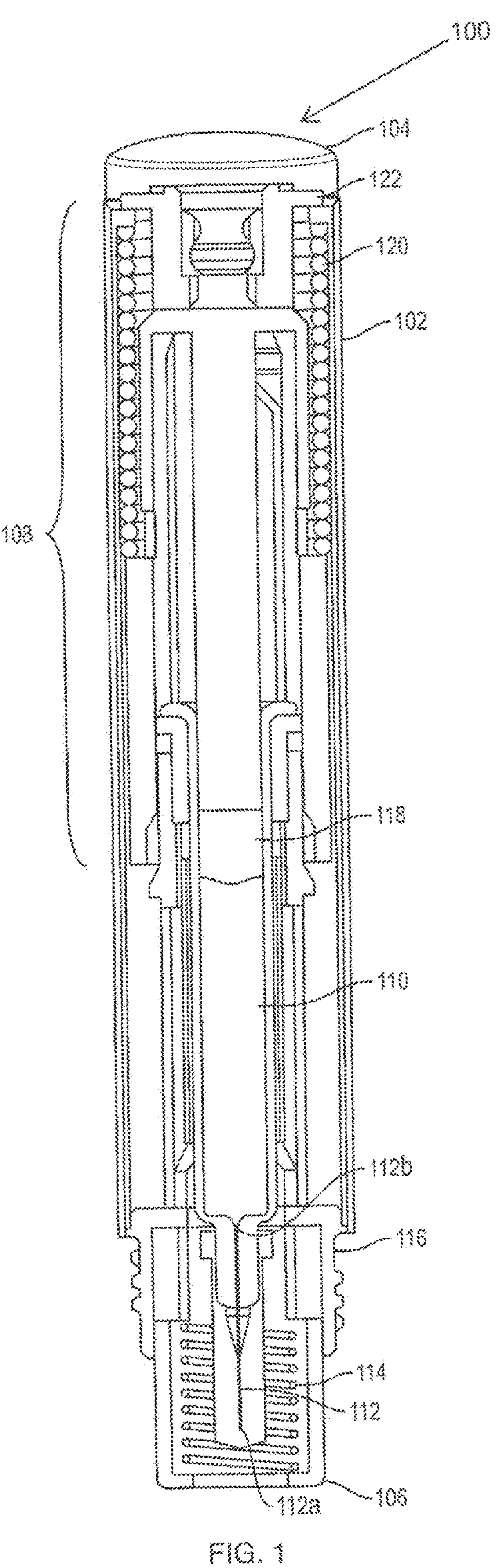
FIG. 1 is a cross-sectional view of an exemplary injection device according to an exemplary embodiment of the present disclosure.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION

With reference to the accompanying drawings, various embodiments of the present invention are described more fully below. Some but not all embodiments of the present invention are shown. Indeed, various embodiments of the invention may be embodied in many different forms and should not be construed as limited to the embodiments expressly described. Like numbers refer to like elements throughout. The singular forms “a,” “an,” and “the” include the singular and plural unless the context clearly dictates otherwise.

FIG. 1 shows an exemplary injection device 100 according to an exemplary embodiment of the present disclosure. It is noted that, in the context of this disclosure, the terms “distal” and “proximal” are used in reference to the position of the injection device relative to a user of the injection device when merely held by a user. Accordingly, a point located distal to a second point would be further from the user (i.e., towards an injection end of the injection device) and vice versa. As shown in the drawings, the exemplary injection device 100 is preferably a needle assisted jet injection device, although a person having ordinary skill in the art will understand alternative embodiments employing certain features herein can be configured as needle-free jet injectors, or as low-pressure auto-injectors or other mechanized injectors. According to certain exemplary embodiments, injection device 100 can be a one-time disposable needle-assisted jet injector with a lock-out feature. For example, injection device 100 can facilitate a jet injection of medicament stored within injection device 100 and can include a locking feature that prevents a user from attempting to use injection device 100 once the medicament has been dispensed. Preferably, the locking feature is activated upon dispensing of the medicament and not upon use of injection device 100. For example, the locking feature can be activated, thus preventing injection device 100 from a subsequent attempted use by a user, even in the case where the injection device was not actually used by a user for an injection, but where a firing mechanism was inadvertently activated (e.g., during transport, handling, etc. of the device) and the medicament was dispensed. Operation of injection device 100, including the locking feature, is described in further detail below.

According to certain exemplary embodiments, injection device 100 can deliver any suitable liquid drug or medicament. Further, injection device 100 can allow the injection to be administered by individuals that do not have formal training (e.g., self-administered or administered by another individual family member or other caregiver who may not be a formally trained healthcare provider, such as a parent administering a drug to a child). Accordingly, injection device 100 can be useful in situations where self-injections/caregiver administered injections would be beneficial, including, but not limited to, low testosterone also known as low T, hypogonadism, diabetes, infertility treatment, sexual dysfunction, cardiovascular disease, oncology, oncology supportive care, allergic reaction, multiple sclerosis, rheumatoid arthritis psoriasis, other autoimmune conditions including Crohn’s disease and SLE, chronic pain, migraine, acute seizure, epileptic seizure, kidney disease, and the like. Further, injection device 100 can be used to inject a wide range of drugs. For example, injection device 100 can be used to inject drugs, water soluble medicaments and oil soluble medicaments. In one embodiment, the medicament includes a benzodiazepine, including midazolam. In another embodiment, the medicament is dissolved in oil instead of aqueous solutions, and can include hormone drugs used in men (e.g., testosterone, or a derivative or ester thereof) and women; small molecule injectable drugs such as, methotrexate (see, e.g., International Publication No. WO 2010/108116, which is incorporated by reference herein in its entirety); and/or biological drugs, including those having a high viscosity. Further, and as noted above injection device 100 can be used to inject androgens, including testosterone formulations (e.g., testosterone cypionate and testosterone enanthate).

Testosterone is a steroid hormone from the androgen group. In general, androgens promote protein synthesis and growth of those tissues with androgen receptors. Testosterone is anabolic, meaning it builds up bone and muscle mass. Testosterone has the following structural formula:

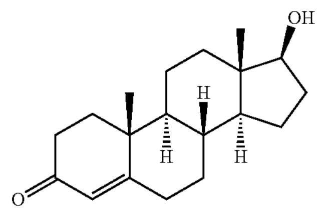

The original and primary use of testosterone is for the treatment of males who have too little or no natural endogenous testosterone production-males with Low T or hypogonadism. According to the Massachusetts Male Aging Study, about 6% to 12% men aged 40 to 60 years have symptomatic low testosterone deficiency. However, over the years, testosterone has also been given for many other conditions, e.g., reducing infertility, correcting lack of libido or erectile dysfunction, correcting osteoporosis, encouraging penile enlargement, encouraging height growth, encouraging bone marrow stimulation, reversing the effects of anemia and appetite stimulation.

In certain embodiments, injection device 100 can be used to inject one or more of epinephrine, atropine, dihydroergotamine, sumatriptan, antibiotics, antidepressants, anticoagulants, glucagon, diazepam, haloperidol, apomorphine, lovenox, and toradol. In other embodiments, injection device 100 can be used to inject biosimilar, biological and or peptide drugs, including without limitation Enbrel, Humira, Lantus, Epogen (Procrit), Neulasta, Aranesp, Avonex, PEGasys, Rebif, Neupogen, Betaseron, Avastin, Remicade, Herceptin, Erbitux, Recombinate, Cerezyme, NovoSeven, Tysabri, Synagis, Copaxone and Kogenate FS.

In other embodiments, injection device 100 can be used to inject parathyroid hormone ("PTH") and various other medications such as exenatide and the like. Injection device 100 can also be used to inject medicaments listed in the Physicians' Desk Reference (PDR®), 67th Edition (2013) (which is herein incorporated by reference in its entirety), and, without limitation, allergens, amebicides and trichomonacides, amino acid preparations, analeptic agents, analgesics, analgesics/antacids, anesthetics, anorexics, antacids, antihelmintics, antialcohol preparations, antiarthritics, antiasthma agents, antibacterials and antiseptics, antiviral antibiotics, anticancer preparations, anticholinergic drug inhibitors, anticoagulants, anticonvulsants, antidiabetic agents, antidiarrheals, antidiuretics, antienuresis agents, antifibrinolytic agents, antifibrotics (systemic), antiflatulents, antifungal agents, antigonadotropin, antihistamines, antihyperammonia agents, anti-inflammatory agents, antimalarials, antimetabolites, antimigraine preparations, antinauseants, antincoplastics, anti-obesity preparations, antiparasitics, anti-parkinsonism drugs, antipruritics, antipyretics, antispasmodics and antichloinergics, antitoxoplasmosis agents, antitussives, antivertigo agents, antiviral agents, biologicals, biosimilars, bismuth preparations, bone metabolism regulators, bowel evacuants, bronchial dilators, calcium preparations, cardiovascular preparations, central nervous system stimulants, cerumenolytics, chelating agents, choleretics, cholesterol reducers and anti-hyperlipemics, colonic content acidifiers, cough and cold preparations, decongestants, diazepam, epinephrine expectorants and combinations, diuretics, emetics, enzymes and digestants, fertility agents, fluorine preparations, galactokinetic agents, general anesthetic, geriatrics, germicides, hematinics, hemorrhoidal preparations, histamine H receptor antagonists, hormones, hydrocholeretics, hyperglycemic agents, hypnotics, immunosuppressives, laxatives, mucolytics, muscle relaxants, narcotic antagonists, narcotic detoxification agents, ophthalmological osmotic dehydrating agents, otic preparations, oxytocics, parashypatholytics, parathyroid preparations, pediculicides, phosphorus preparations, premenstrual therapeutics, psychostimulants, quinidines, radiopharmaceuticals, respiratory stimulants, salt substitutes, scabicides, sclerosing agents, sedatives, sympatholytics, sympathomimetics, thrombolytics, thyroid preparations, tranquilizers, tuberculosis preparations, uricosuric agents, urinary acidifiers, urinary alkalinizing agents, urinary tract analgesic, urological irrigants, uterine contractants, vaginal therapeutics and vitamins and each specific compound or composition listed under each of the foregoing categories in the PDR®. Some other medicaments that can be used with injector device 100 include Ergocalciferol (Calciferol), diethylstilbestrol, Diprovan (propofol), estradiol valerate, fluphenazine decanoate, fulvestrant, intralipid, liposyn, nandrolone decanoate, nebido, nutralipid, paclitaxel, progesterone, prograf, testosterone cypionate, zuclopenthixol, and haloperidol dodecanoate. In certain embodiments, the medicament is dissolved in soybean oil, ethyl oleate, castor oil, sesame oil, safflower oil, *arachis* oil, polyoxyyethylated castor oil (Cremophor® EL), polyoxyl 60 hydrogenated castor oil (HCO-60), cottonseed oil, or thin oil derived from coconut oil.

In some embodiments, the medicament may be a hazardous agent. "Hazardous Agent(s)" as used herein means any one or more medications that are toxic agents, cytotoxic agents and/or other dangerous agents that may cause serious effects upon contact with a subject as well as highly potent agents, agents that have profound physiological effects at low doses. Exemplary hazardous agents include, without limitation, analgesics, immunomodulating agents, IL-1 receptor antagonists, IL-2 alpha receptor antagonists, anti-rejection compounds, hormonal agents, prostaglandins, sedatives, anticholinergic agents, Parkinsons disease drugs, expensive agents, neuroleptic agents, tissue necrosis factor (TNF) blockers, and other dangerous agents. Examples of hazardous agents suitable for use with injection device 100 in accordance with the present invention include, but are not limited to, those disclosed in U.S. Patent Application Publication No. 2012/0157965 entitled "Hazardous Agent Injection System" (to Paul Wotton et. al, published Jun. 21, 2012), which is incorporated by reference herein in its entirety. Particular examples of cytotoxic agents include, without limitation, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, and derivatives thereof. Examples of highly potent agents include, without limitation, steroids such as dexamethasone, progesterone, somatostatin, and analogues thereof; biologically active peptides such as teriparatide; and anticholinergics such as scopolamine. Examples of agents that have profound physiological effects at low doses include, without limitation, antihypertensives and/or blood pressure down regulators. Examples of analgesics include, without limitation, fentanyl, fentanyl citrate, morphine, meperidine, and other opioids. Examples of immunomodulating agents include, without limitation, adalimumab (anti-tissue necrosis factor monoclonal antibody or anti-TNF). Examples of IL-1 receptor antagonists include, without limitation, anakinra. Examples of IL-2 alpha receptor antagonists include, without limitation, daclizumab and basiliximab. Examples of anti-rejection compounds include, without limitation, azathioprine, cyclosporine, and tacrolimus. Examples of hormonal agents include, without limitation, testosterone, estrogen, growth hormone, insulin, thyroid hormone, follicle stimulating hormone (FSH), epinephrine/adrenaline, progesterone, parathyroid hormone, gonadotrophin releasing hormone (GHRH), leutinizing hormone releasing hormone (LHRH), other hormones such as those where contact with the hormone by members of the opposite sex can lead to side effects, and derivatives thereof. Examples of prostaglandins include, without limitation, gamma-linolenic acid, docosahexanoic acid, arachidonic acid and eicosapentaenoic acid. Examples of sedatives include, without limitation, barbiturates such as amobarbital, pentobarbital, secobarbital, and phenobarbital; benzodiazepines such as clonazepam, diazepam, estazolam, flunitrazepam, lorazepam, midazolam, nitrazepam, oxazepam, triazolam, temazepam, chlordiazepoxide, and alprazolam; herbal sedatives such as ashwagandha, *Duboisia hopwoodii*, prosanthera *striatiflora*, kava (*Piper methysticum*), mandrake, valerian, and marijuana; non-benzodiazepine sedatives (a.k.a. "Z-drugs") such as eszopiclone, zaleplon, zolpidem, zopiclone; antihistamines such as diphenhydramine, dimenhydrinate, doxylamine, and promethazine; and other sedatives such as chloral hydrate. Examples of anticholinergic agents include, without limitation, dicyclomine, atropine, ipratropium bromide, oxitropium bromide, and tiotropium. Examples of Parkinson's disease drugs include, without limitation, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, and lisuride. Examples of expensive agents include, without limitation, human growth hormone and erythropoietin. Examples of neuroleptic agents includes, without limitation, antipsychotics; butyrophenones such as haloperidol and droperidol; phenothiazines such as chlorpromazine, fluphenazine, perphenazine, prochlorperazine, thioridazine, trifluoperazine, mesoridazine, periciazine, promazine, triflupromazine, levomepromazine, promethazine, and pimozide; thioxanthenes such as chlorprothixene, clopenthixol, flupenthixol, thiothixene, and zuclopenthixol; atypical antipsychotics such as clozapine, olanzapine, risperidone, quetiapine, ziprasidone, amisulpride, asenapine, paliperidone, iloperidone, zotepine, and sertindole; and third generation antipsychotics such as aripiprazole and bifeprunox. Examples of TNF blockers includes, without limitation, etanercept.

In some embodiments, the hazardous agent can be selected from botulinum toxin, injectable gold, 6-mercaptopurine, 6-thioinosinic acid, azathioprine, chlorambucil, cyclophosphamide, cytophosphane, cytarabine, fluorouracil, melphalan, methotrexate, uramustine, anti-cytokine biologicals, cell receptor antagonists, cell receptor analogues, dexamethasone, progesterone, somatostatin, analogues of dexamethasone, analogues of progesterone, analogues of somatostatin, teriparatide, scopolamine, antihypertensives, blood pressure down regulators, fentanyl, fentanyl citrate, morphine, meperidine, other opioids, adalimumab (anti-tissue necrosis factor monoclonal antibody or anti-TNF), anakinra, daclizumab, basiliximab, azathioprine, cyclosporine, tacrolimus, testosterone, estrogen, growth hormone, insulin, thyroid hormone, follicle stimulating hormone (FSH), epinephrine/adrenaline, gamma-linolenic acid, docosahexanoic acid, arachidonic acid, cicosapentaenoic acid, amobarbital, pentobarbital, secobarbital, phenobarbital, clonazepam, diazepam, estazolam, flunitrazepam, lorazepam, midazolam, nitrazepam, oxazepam, triazolam, temazepam, chlordiazepoxide, alprazolam, ashwagandha, *Duboisia hopwoodii*, prosanthera striatiflora, kava (*Piper methysticum*), mandrake, valerian, marijuana, eszopiclone, zaleplon, zolpidem, zopiclone, diphenhydramine, dimenhydrinate, doxylamine, promethazine, chloral hydrate, dicyclomine, atropine, ipratropium bromide, oxitropium bromide, tiotropium, levodopa, dopamine, carbidopa, benserazide, co-ceraldopa, co-beneldopa, tolcapone, entacapone, bromocriptine, pergolide, pramipexole, ropinirole, piribedil, cabergoline, apomorphine, lisuride, human growth hormone, erythropoietin, haloperidol, droperidol, chlorpromazine, fluphenazine, perphenazine, prochlorperazine, thioridazine, trifluoperazine, mesoridazine, periciazine, promazine, triflupromazine, levomepromazine, promethazine, pimozide, chlorprothixene, clopenthixol, flupenthixol, thiothixene, zuclopenthixol, clozapine, olanzapine, risperidone, quetiapine, ziprasidone, amisulpride, asenapine, paliperidone, iloperidone, zotepine, sertindole, aripiprazole, bifeprunox, etanercept, derivatives of any of the foregoing, and combinations of any of the foregoing.

While injection device 100 can deliver an injection of up to about 3 mL per injection, other volumes can be injected in alternative embodiments. In certain embodiments, injection device 100 can deliver an injection of greater than 1 mL per injection. In other embodiments, injection device 100 can deliver an injection in range of about 1 mL to about 3 mL.

According to certain exemplary embodiments, injection device 100 can be configured to inject medicament stored within a prefilled syringe. Prefilled syringes that are manufactured by a blown glass process can have significant dimensional tolerances and unevenness. Accordingly, features of injection device 100 can serve to accommodate the shape irregularities and to properly position and locate a prefilled syringe within injection device 100. Other medicament containers such as prefilled syringes manufactured with polymers can also be accommodated. Further, injection device 100 can be configured as a needle-assisted jet injector, providing a peak pressure during the injection of less than about 1,000 p.s.i., preferably less than 500 p.s.i., and more preferably less than about 350 p.s.i. At an end of an injection, the pressure applied to the medicament is preferably at least about 80 p.s.i., more preferably at least about 90 p.s.i., and most preferably at least about 100 p.s.i. In one embodiment, the initial pressure can be around 330 p.s.i., and the final pressure can be about 180 p.s.i., while in another embodiment the initial pressure can be about 300 p.s.i., dropping to around 110 p.s.i. at the end of the injection. These exemplary pressures can, for example, result in a flow rate of about 0.2 mL/sec to 0.75 mL/sec, and preferably about 0.5 mL/sec. In one embodiment, the rate is greater than 0.2 mL/sec. In one embodiment, the injection device 100 may include an energy source 120, e.g., a high force spring, such as those needed for rapid ejection of difficult to eject medicaments. High force springs may be desired in situations where rapid delivery of drugs is important to assure injection of the entire dose; this would be to counteract users removing the injector from the injection site prematurely. Medicaments can be difficult to eject due to either high viscosity or because of a combination of their viscosity and a therapeutic need for delivery of the medicament using fine bore needles, such as the 29 gauge prefilled syringe.

The needles used may be between 25 and 29 gauge. The needles used are preferably between 26 and 28 gauge, and are most preferably around 27 gauge, but alternatively other needle gauges can be used where the other components are cooperatively configured to produce the desired injection. In preferred jet injector embodiments firing aqueous medicaments, the firing mechanism, medicament container, needle, and energy source are configured to produce an average stream velocity within the needle of at least about 1,000 cm/sec, and more preferably at least about 1,500 cm/sec, up to about 5,000 cm/sec, and more preferable up to about 3,000 cm/sec. In one embodiment, the average stream velocity during injection is about or reaches between about 1,800 and 2,200 cm/sec or approximately 2,000 cm/sec. The velocities used to produce a jet injection will vary for other types of medicaments, such as based on their viscosities. Weaker energy sources, and/or larger needles, for example, can be used to obtain lower velocities and lower pressures and/or flow rates for traditional, low-pressure autoinjector embodiments. Such embodiments can also benefit from the axial rotation between the trigger engagement member and the retaining portion, while moving from the pre-firing condition to the firing condition upon a proximal movement of the skin-contacting member with respect to housing. An example of which, but not limited to, is a reduction of friction between spring loaded components.

As shown in FIG. 1, the exemplary injection device 100 can include an outer housing 102 and a housing end/end cap 104. Injection device 100 can further include various components and/or assemblies housed within outer housing 102. As shown in FIG. 1, these components can include a guard 106, a container support, such as, e.g., a sleeve 116, a firing mechanism 108, a medicament chamber 110, a needle 112, and a spring 114. As shown in FIG. 1, outer housing 102 can be a single piece component, or alternatively, outer housing 102 multiple piece assembly that can be coupled together, for example, via a snap-fit connection, a press-fit connection, a threaded engagement, adhesives, welding, or the like.

Figure 7B:
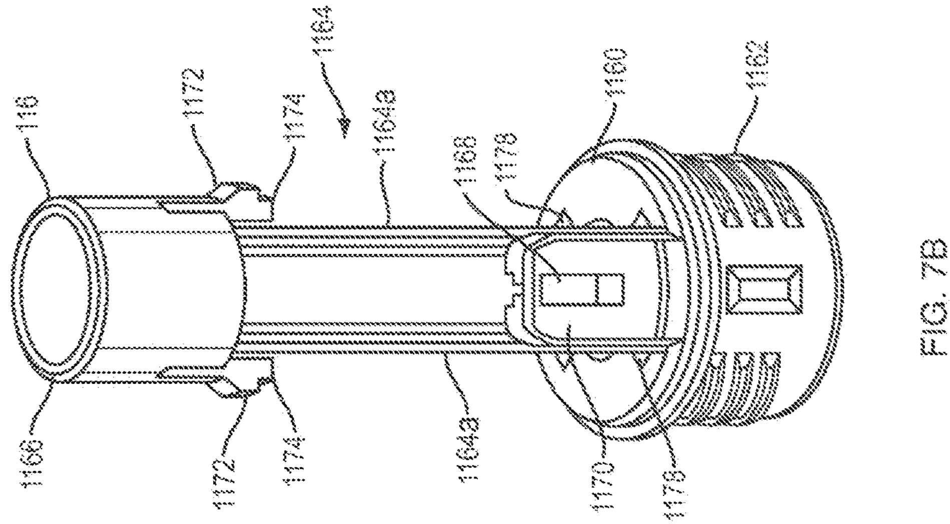
FIGS. 7A and 7B are side and perspective views respectively of a front housing portion and a sleeve of an exemplary injection device according to an exemplary embodiment of the present disclosure.
Figure 7A:
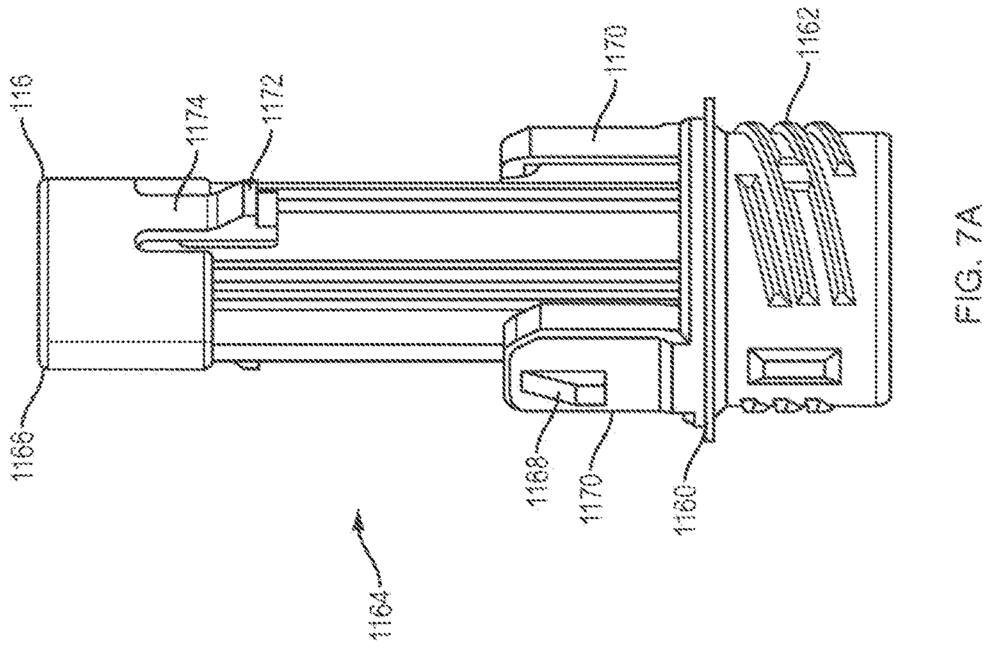

As shown in FIG. 1, sleeve 116 is preferably at least partially housed within outer housing 102 and mounted to outer housing 102 via, for example, a snap-fit connection, a press-fit connection, a threaded engagement, adhesives, welding, or the like. As shown in FIGS. 7A and 7B, for example, sleeve 116 can include projections 1168 configured to engage openings of housing 102. Sleeve 116 is configured to hold a medicament chamber 110, which can include a needle 112 at a distal end of medicament chamber 110. In certain exemplary embodiments, medicament chamber 110 can include, for example, a separate glass ampule and a needle, or a pre-filled syringe, or sleeve 116 itself can include an integral medicament chamber. Preferably, a plunger 118 is provided in the medicament chamber 110. Plunger 118 is in association with a ram 1232 of firing mechanism 108. During an injection, ram 1232 is urged by an energy source of firing mechanism 108 to displace plunger 118 distal, deeper into medicament chamber 110, dispensing the medicament through needle 112. Needle 112 can include an injecting tip 112*a* that can be configured to penetrate the skin of a user and a hollow bore 112*b* that is in fluid communication with medicament chamber 110 to facilitate delivery of medicament from medicament chamber 110 to a user during an injection. FIG. 1 shows injection device 100 in a pre-firing state. The operation of injection device 100, including its various stages and positions, are described in further detail below.

As also shown in FIG. 1, injection device 100 also preferably includes firing mechanism 108. Firing mechanism 108 can include a ram assembly 122 slidably mounted within housing 102 and an energy source 120. In an exemplary embodiment, the energy source 120 preferably includes a compression spring 120, however, other suitable energy source can be used, such as an elastomer or compressed-gas spring, or a gas generator, or other suitable energy storage members. In FIG. 1, ram assembly 122 is in a pre-firing proximal-most position. During an injection, ram assembly 122 is urged distally by energy released by energy source 120. Once an injection is completed, firing ram assembly 122 is disposed in a distal position. In this distal position, guard 106 is locked-out so that a user cannot attempt a subsequent injection. Although shown as a single piece, ram assembly 122 can be a multiple piece assembly that can be coupled together, for example, via a snap-fit connection, a press-fit connection, a threaded engagement, adhesives, welding, or other suitable couplings. Ram assembly 122 preferable includes various features that can be configured to facilitate firing of injection device 100 to dispense the medicament stored in medicament chamber 110. According to certain exemplary embodiments of the present disclosure, a trigger mechanism of injection device 100 can include ram assembly 122, the floating trigger member 300, which can include a retaining portion 306, and ram retaining holding member 1042.

Figure 2:
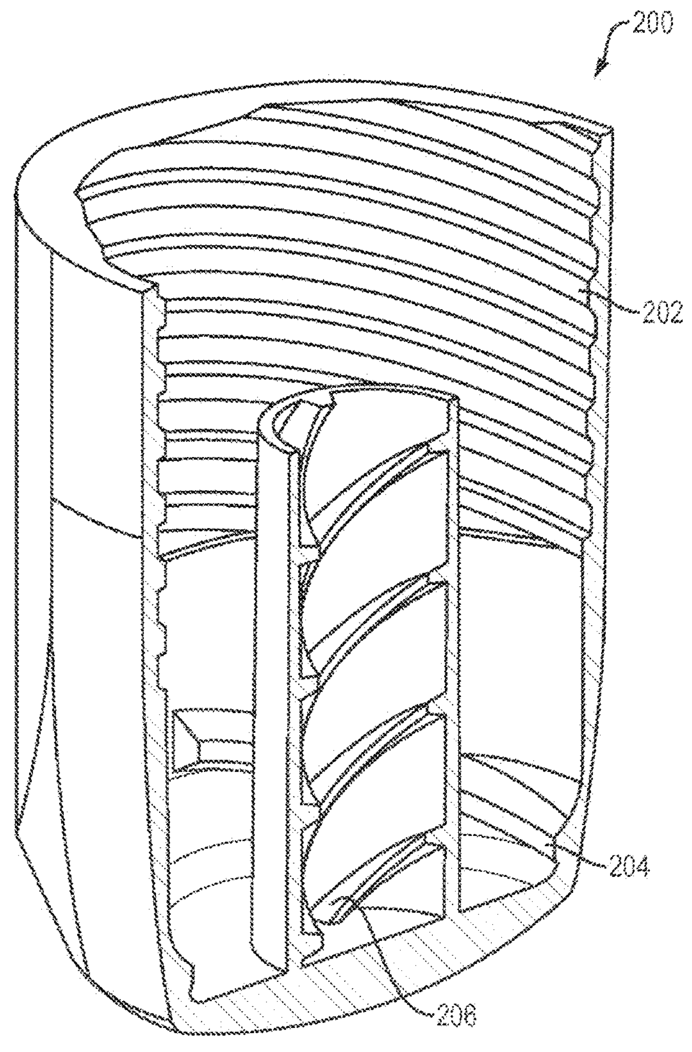
FIG. 2 shows a cross sectional view of a cap of an exemplary injection device according to an exemplary embodiment of the present disclosure.

In one embodiment, injection device 100 includes a cap 200, as shown in FIG. 2. The cap 200 may be removably affixable to a distal end of outer housing 102. In another embodiment, the housing end/end cap 104 is coupled to a proximal end of housing 102. For example, cap 200 can be removably affixed to the distal end of housing 102 via a threaded engagement and housing end/end cap 104 can include features (e.g., projections) configured to engage a portion of the proximal end of housing 102 (e.g., openings) to couple housing end/end cap 104 to housing 102. When affixed to injection device 100, the cap 200 can ensure that an injection is not triggered by an inadvertent application of a force to guard 106. Preferably, the cap 200 includes two engagement features. As shown in FIG. 2, the cap 200 can include engagement features 202 and 204. Engagement features 202 and 204 can be threads configured to threadedly engage other features of injection device 100. For example, engagement feature 202 can be configured to secure cap 200 to the distal end of housing 102 (e.g., via a threaded engagement with a distal portion of sleeve 116), and engagement feature 204 can be configured to threadedly engage features of guard 106 to prevent proximal displacement of guard 106.

Additionally, cap 200 is any regular or irregular shape and can be non-circular in cross-section viewed along its axis and in the initial, closed position aligns with or substantially matches the shape of the portion of the housing adjacent thereto. Features 202 and 204 can include a plurality of threads, having more than one thread starting point, only one of which will result in the cap lining up with the housing as in the initial closed position. Consequently, if the cap is removed and replaced, there is a chance that an incorrect starting point will be selected by the user, resulting in the cap no longer aligning with the injector housing, and providing an indication of tampering. In one embodiment, three threads are used, so there is a two in three chance that a removed and replaced cap will become immediately obvious based on an ill-fitting cap.

Housing 102 can also include openings configured to engage with sleeve 116 to couple and secure sleeve 116 to housing 102 and can include at least one window that can provide a visual indication of whether or not injection device 100 has been fired. For example, in an unfired state, the window can allow a user to see medicament chamber 110, along with the stored medicament, and in a fired state, the window can show one or more internal components, such as a portion of firing mechanism 112, which can be a color specifically selected to alert the user that injection device 100 has been fired, and is preferably sufficiently different than other colors visible to a user (preferably having ordinary eyesight) on the injector prior to firing, so as to be conspicuously different to, or contrast from, any other colors present or significantly present. For example, the color can differ from all the other components of injection device 100 pre-firing, or visible by the user pre-firing, so as to be conspicuous (e.g., introducing an entirely new color family). The new color appearing after firing, can be from a non-analogous part of the color wheel, or can contrast, or can be a complementary color, with respect to the colors visible on injection device 100. The new color can signify caution, such as red or orange, etc. In one embodiment, the colors visible on the injector in the pre-firing condition, preferably including when the cap 200 is on and/or off the injector, are grays and blues, for instance. When the injector is fired, the color red can be introduced. Preferably, this new color can be introduced after firing but prior to guard 106 being locked-out in the extended position.

Figure 3A:
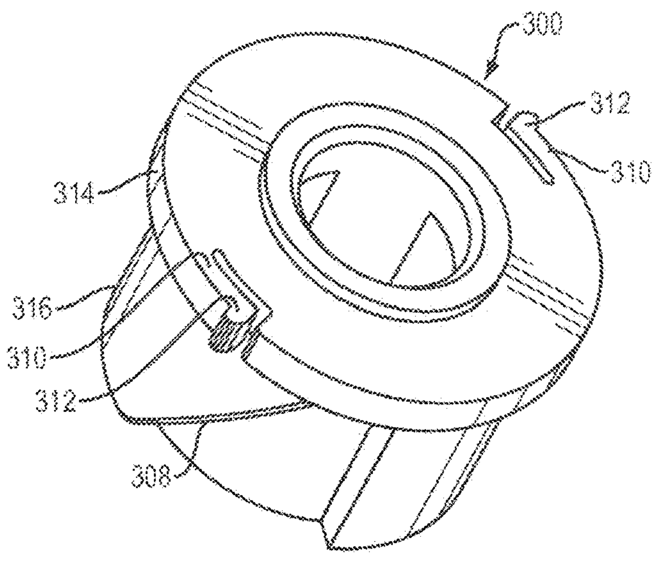
FIG. 3A is a perspective view of a floating trigger member of an exemplary injection device according to an exemplary embodiment of the present disclosure.
Figure 3B:
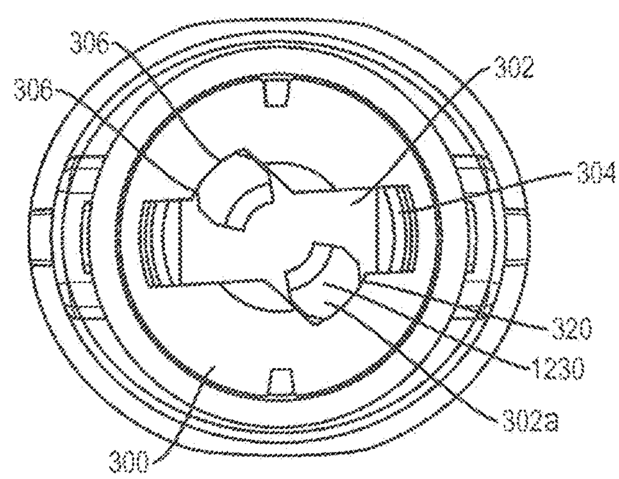
FIG. 3B is a cross-section view of an exemplary injection device according to an exemplary embodiment of the present disclosure in a retaining position.
Figure 3C:
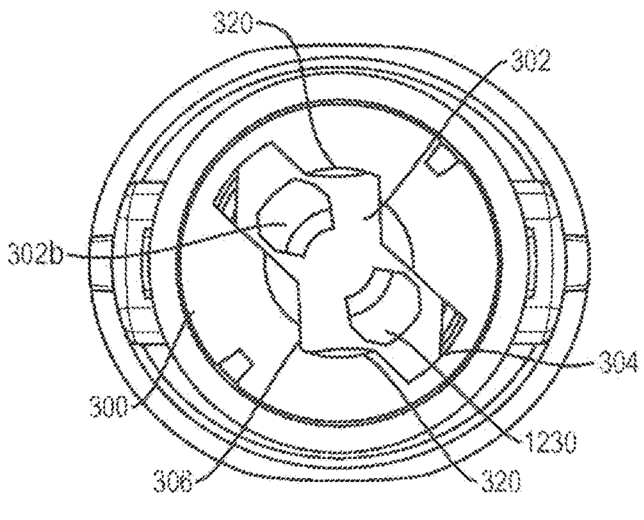
FIG. 3C is a cross-section view of an exemplary injection device according to an exemplary embodiment of the present disclosure in a firing position

In one embodiment, the injection device 100 includes a floating trigger member 300, as shown in FIGS. 3A, 3B and 3C. The floating trigger member 300 can have a proximal portion 314 and a distal portion 316. Further, the floating trigger member 300 can include an opening 302 in the distal portion 316. The opening 302 can include a retaining portion 306 configured to receive and engage at least a trigger engagement member of firing mechanism 108 (e.g., projections) in facilitating firing of injection device 100. The opening 302 is preferably configured to engage a trigger engagement member, e.g., projections 1230 of firing mechanism 108, for example latch tabs, such that they are aligned in one of two positions. For example, in first position 302*a* (e.g., retaining position), projections 1230 of firing mechanism 108 are aligned so that they can be restrained by the retaining portion 306, thereby preventing firing mechanism 108 from firing and dispensing the medicament. In second position 302*b* (e.g., firing position), the opening 302 can include firing portions 304 such that the projections 1230 of firing mechanism 108 are aligned such that projections can splay apart, thereby permitting firing mechanism 108 to fire. FIG. 3B shows projections 1230 aligned in the first position (302*a*) and FIG. 3C shows projections 1230 aligned in the second position (302*b*). Further, the retaining portion 306 of the opening 302 (e.g., in the first position 302*a*) is preferably curved to facilitate rotation of the floating trigger member from the first and second positions. An exterior surface of distal portion 316 of the floating trigger member 300 can include camming surfaces 308. In one embodiment, a portion of projections 1230 optionally engage rests 320, such that when floating trigger member 300 rotates, projection 1230 disengage rests 320 allowing firing mechanism 108 to fire.

Figures 6A, 6B:
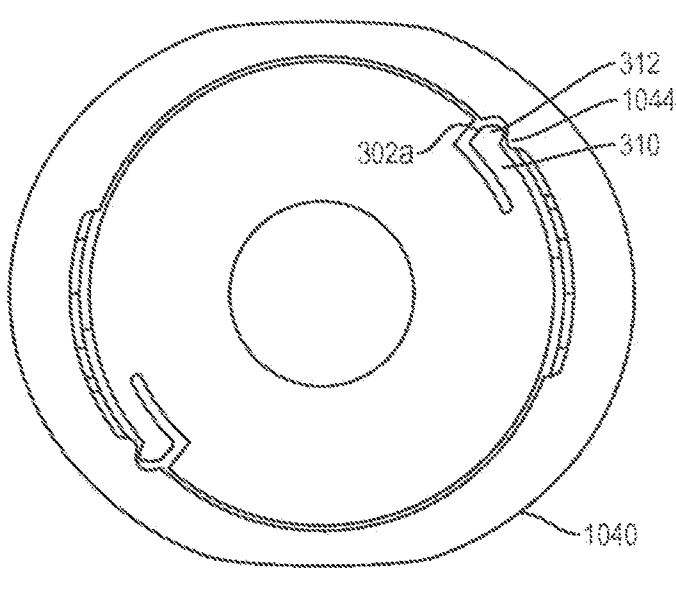
FIG. 6A is a cross-section view of an end housing portion and floating trigger member of an exemplary injection device according to an exemplary embodiment of the present disclosure in a retaining position.
FIG. 6B is a cross-section view of an end housing portion and floating trigger member of an exemplary injection device according to an exemplary embodiment of the present disclosure in a firing position.

The proximal portion 314 of the floating trigger member can include flanges 310 having lips 312, described further below with reference to FIG. 6.

Figure 4:
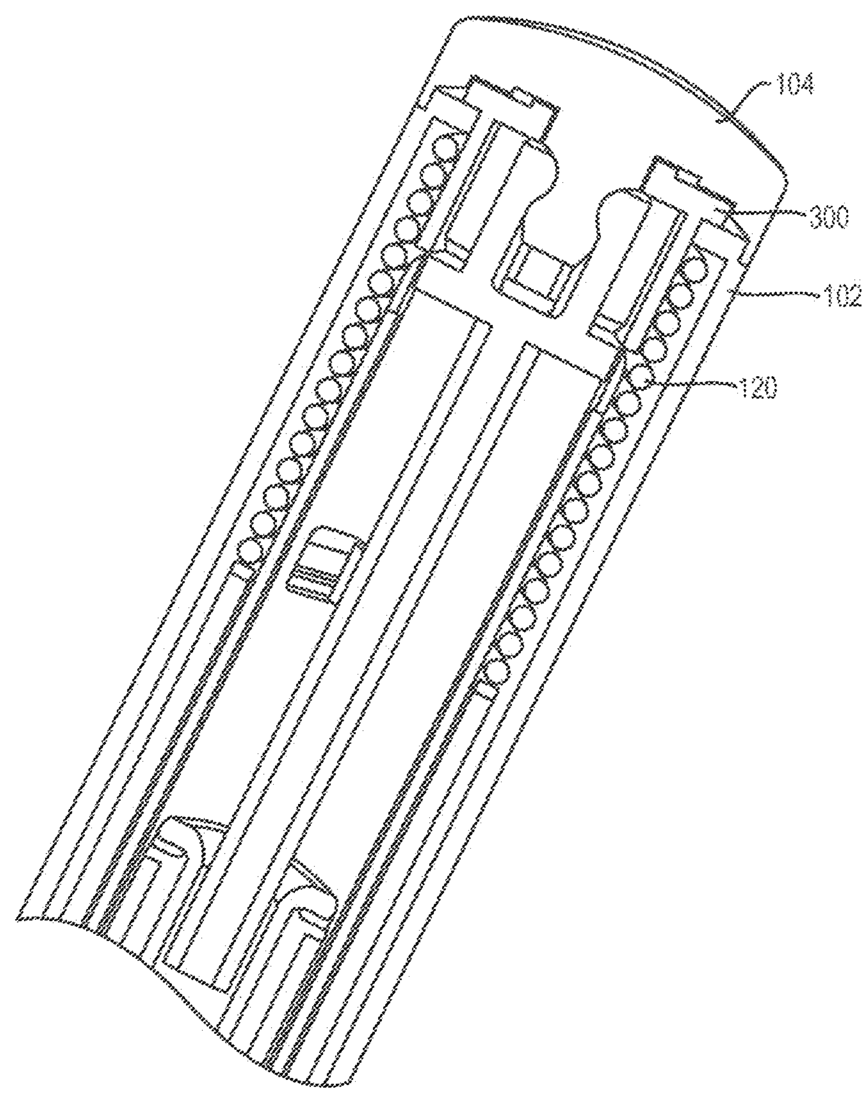
FIG. 4 is a cross-sectional view of an exemplary injection device according to an exemplary embodiment of the present disclosure.

As shown in FIG. 4, energy source 120 (e.g., a spring) is decoupled from guard 106. Instead, the proximal end energy source 120 is coupled to housing 102. By decoupling energy source 120 from guard 106, the apparent friction of rotation of floating trigger member 300 is significantly reduced. This in turn substantially reduces the amount of force necessary to move guard 106 from an extended position to the firing position as described with reference to FIGS. 9A and 9B, below. Specifically, the compression of components caused by energy source 120 is substantially eliminated thereby significantly reducing the amount of apparent friction and resistance to movement of guard 106 during use of injection device 100.

Figure 5:
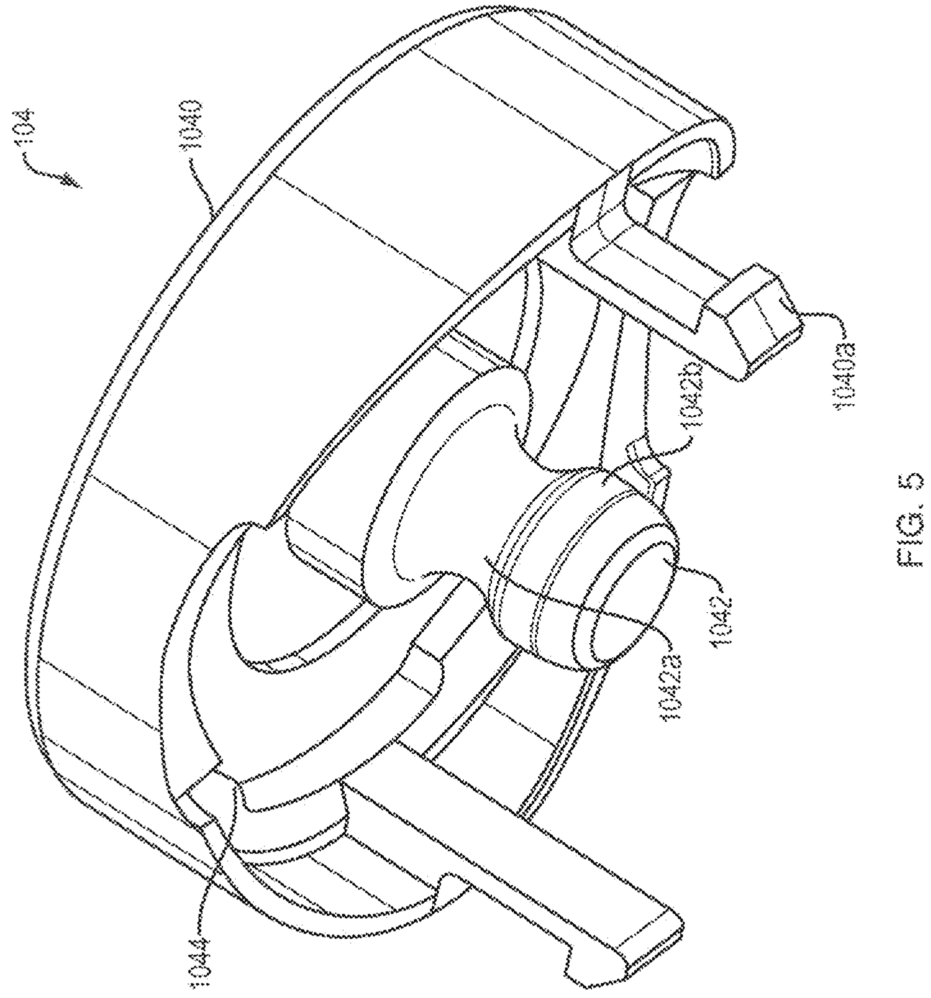
FIG. 5 is a prospective view of an end housing portion of an exemplary injection device according to an exemplary embodiment of the present disclosure.

Injection device 100 also preferably includes housing end/end cap 104. As shown in FIG. 5, housing end/end cap 104 preferably includes a body portion 1040 and a ram holding member 1042. Ram holding member 1042 can be a projection, and can be configured to engage a trigger engagement member of firing mechanism 108. For example, ram holding member 1042 can be a bell-shaped projection, and can engage a complementary shaped feature (e.g., projections) of firing mechanism 108. In an exemplary embodiment, ram holding member 1042 can include a groove 1042*a* and a bulge 1042*b*, and features of firing mechanism 108 can be configured to align with groove 1042*a* so as to hold bulge 1042*b* to prevent firing of injection device 100. Preferably, ram holding member 1042 and the features of firing mechanism 108 engaging with ram holding member 1042 include a circular cross section to allow rotation of the features of firing mechanism 108 relative to ram holding member 1042 during firing of injection device 100. Further, body portion 1040 can include projections 1040*a* configured to engage openings in outer housing 102 to couple housing end/end cap 104 to housing 102.

In an exemplary embodiment, the housing end/end cap 104 optionally includes an engagement member 1044, as shown in FIG. 5. As further detailed in FIGS. 6A and 6B, the engagement member 1044 engages lip 312 of the floating trigger member 300 when the floating trigger member 300 is rotated from the first position to the second position. In certain embodiments having engagement member 1044 and lip 312, a threshold breakaway force is needed to overcome the resistance on the floating trigger member caused by the engagement portion 1044 when the floating trigger member is moved at least partially from the first position to the second position. The breakaway feature serves as a safety to prevent unintended rotation of the floating trigger member. As shown in FIGS. 7A and 7B, sleeve 116 can include a ring-like structure 1160, a coupling arrangement 1162, and a body portion 1164. Coupling arrangement 1162 can be disposed at a distal portion of sleeve 116 and can be configured to releasably engage cap 200. For example, coupling arrangement 1162 can include threads configured to provide threaded engagement between sleeve 116 and cap 200. Further, sleeve 116 can include a body portion 1164 configured to secure medicament chamber 110. Body portion 1164 can include guides, such as grooves 1164*a*, configured to engage with features of guard 106 to align and guide axial displacement of guard 106. A proximal end of sleeve 116 can include a medicament chamber support 1166 configured to support and secure a proximal portion of medicament chamber 110. For example, support 1166 can be configured as a syringe support configured to hold a proximal end of syringe (e.g., finger flanges of a prefilled syringe) and can support medicament chamber 110 during the forces exerted on it during firing. Further, support 1166 can include an elastomer or a rubber, and can be configured to at least partially absorb the shock or a force exerted on medicament chamber 110 during an injection. Additionally, sleeve 116 can include various features, such as projections 1168, configured to couple sleeve 116 to outer housing 102. For example, projections 1168 can be concentrically symmetrical and configured to engage openings in outer housing 102 to secure sleeve 116 to outer housing 102. In an exemplary embodiment, projections 1168 can be disposed on legs 1170, which can be concentrically symmetrical and configured to engage with features of guard 106. Additionally, sleeve 116 can include locking features, such as locking projections 1172, disposed on legs 1174, which can be concentrically symmetrical, and can be configured to engage firing mechanism 108 in locking out injection device 100 to prevent a user from attempting to use an already-fired injection device 100.

Ring-like structure 1160 can include several features configured to engage sleeve 116 with glass medicament chamber 110, firing mechanism 108, and guard 106. For example, ring-like structure 1160 can include an opening 1166 through which needle 112 can be received. Further, ring-like structure 1160 can include concentrically symmetrical openings 1178 which can be configured to receive legs of guard 106. Additionally, ring-like structure 1160 can be configured to support a distal portion of medicament chamber 110 and engage firing mechanism 108 in preventing further axial displacement of firing mechanism 108 during dispensing of the medicament. Operations of these components are described in further detail below.

Figure 8:
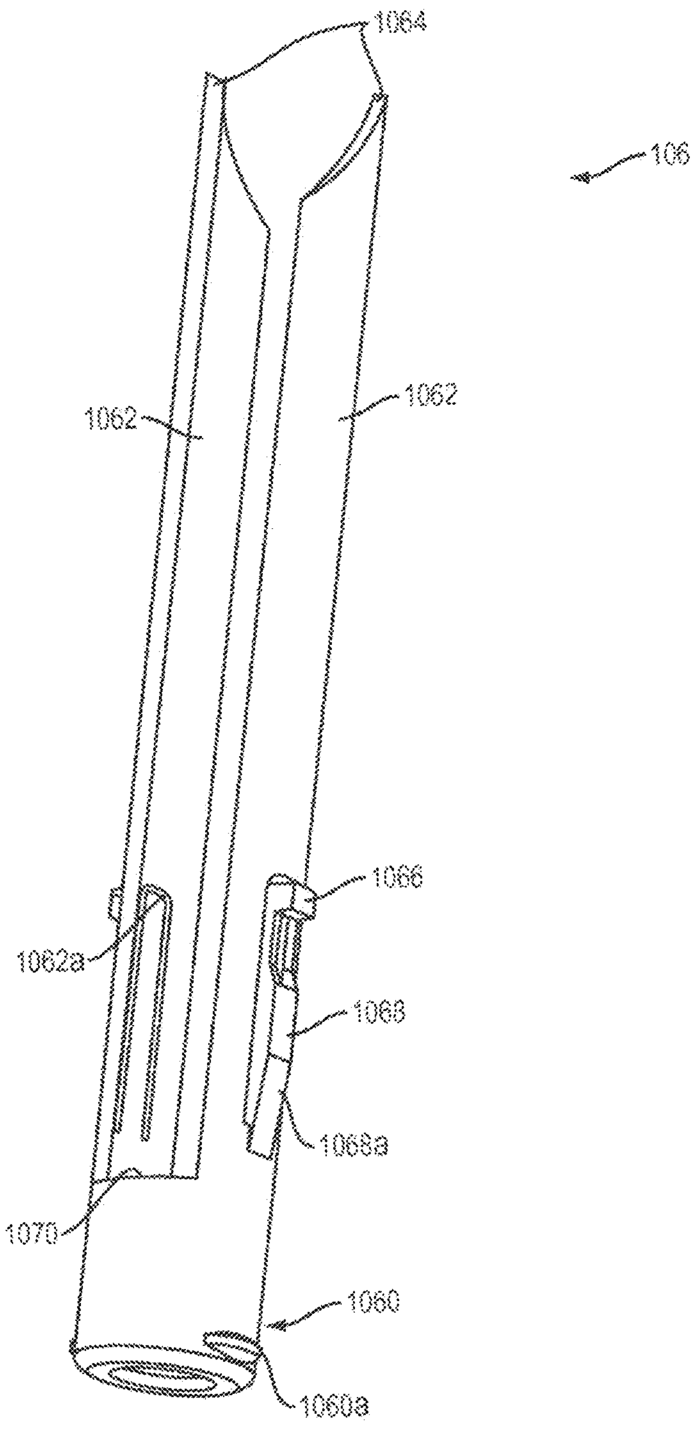
FIG. 8 is a side and perspective views of a needle guard of an exemplary injection device according to an exemplary embodiment of the present disclosure.
Figure 9B:
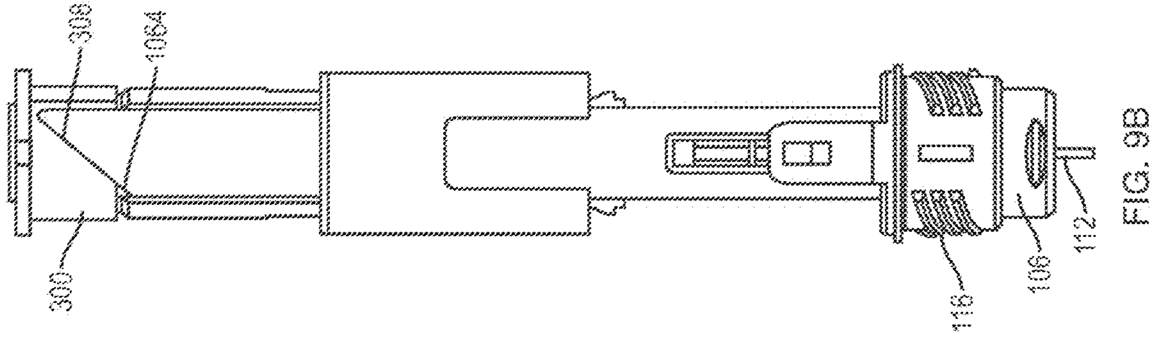
FIGS. 9A and 9B are side views of a ram assembly, needle guard, floating trigger member, sleeve an of an exemplary injection device according to an exemplary embodiment of the present disclosure in unfired and fired positions, respectively.
Figure 9A:
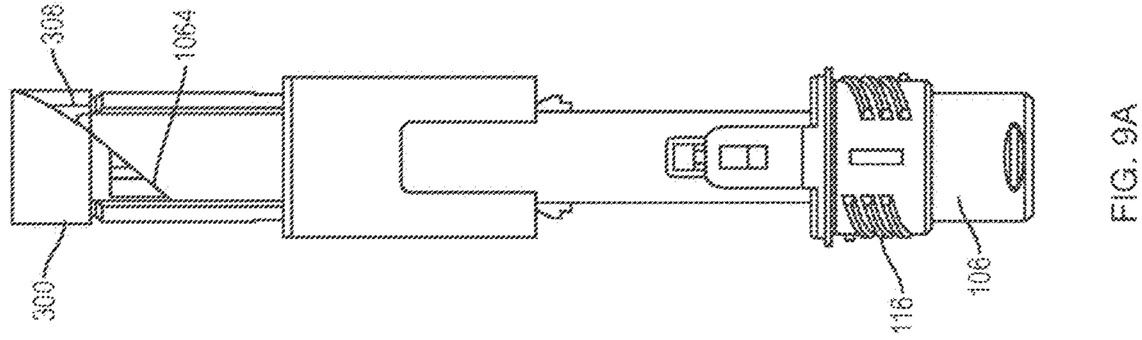

As shown in FIG. 8, injection device 100 preferably includes a guard 106 slidably mounted at least partially within outer housing 102 and configured to engage firing mechanism 108 to actuate firing of injection device 100. Preferably, guard 106 is slidably movable relative to outer housing 102 between an extended (e.g., a distal, protective) position and a retracted (e.g., proximal) position. In the extended position, guard 106 preferably covers needle 112, and in the retracted position, needle 112 is not covered by guard 106 and is thereby exposed. For example, FIG. 9A shows guard 106 in the extended position, and FIG. 9B shows guard 106 in the retracted position. Preferably, guard 106 is resiliently biased toward the extended position via a spring 114, which can be disposed, for example, between a distal surface of ring-like structure 1160 of sleeve 116 and an interior surface of a distal end of guard 106.

In an exemplary embodiment, guard 106 includes a distal portion 1060 and legs 1062. In an exemplary embodiment, the distal end of guard 106 preferably includes a skin-contacting member. Distal portion 1060 includes an opening through which needle 112 can pass and projections 1060*a*. In an exemplary embodiment, projections 1060*a* can be configured to engage engagement features 202 and 204 of cap 200 so that guard 106 cannot be proximally displaced when engaged with engagement features 202 or 204 of cap 200. In an exemplary embodiment, the guard 106 includes a stop surface 1070. In an exemplary embodiment, the stop surface 1070 can be configured to abut an inside surface of the ring like structure 1160 of sleeve 116 so as to limit the proximal displacement of guard 106. For example, as guard 106 is proximally displaced under a force applied by a user during an injection, stop surface 1070 will come into contact with the inside surface of the ring like structure 1160 of sleeve 116 so that guard 106 cannot be further proximally displaced.

Legs 1062 of guard 106 are preferably configured to be received in openings 1178 of ring-like structure 1160. Further, legs 1062 can include ridges 1062*a* configured to engage grooves 1164*a* of sleeve 116, to facilitate alignment and guiding of legs 1062 as guard 106 is axially displaced. As shown in the exemplary embodiment of FIG. 8, legs 1062 also preferably include firing-initiation members, such as camming surfaces 1064 at a proximal end of legs 1062. In an exemplary embodiment, legs 1062 and camming surface 1064 can be concentrically symmetrical. Camming surfaces 1064 are configured to engage firing mechanism 108 in initiating a firing of injection device 100 and performing an injection of the medicament stored in medicament chamber 110. The proximal ends of legs 1062 can also be sloped to facilitate legs 1062 being received within firing mechanism 108 when guard 106 is displaced from the extended position to the retracted position. In an exemplary embodiment, the camming surfaces 1064 are configured to engage camming surfaces 308 of the floating trigger member 300. Preferably, legs 1062 include projections 1066 disposed on springs 1068 which can also include sloped surfaces 1068*a*. Projections 1066 can be configured to engage proximal surfaces of legs 1170 of sleeve 116 to oppose a force exerted by spring 114, which biases guard 106 in the extended position. Further, sloped surfaces 1068*a* can be configured to engage an interior surface of legs 1170 of sleeve 116 so that as guard 106 is displaced from the extended position to the retracted position, sloped surfaces 1068*a* engage the interior surfaces of legs 1170 so as to bias springs 1068 towards an interior of injection device 100.

FIG. 9A shows engagement of camming surfaces 1064 of the guard with camming surfaces 308 of the floating trigger member 300 in a pre-fired state. FIG. 9B shows engagement of camming surfaces 1064 of the guard with camming surfaces 308 of the floating trigger member 300 in a fired state. As guard 106 is moved in the proximal direction, the axial movement of guard 106 is translated into a rotational movement of the floating trigger member 300 via the engagement of camming surfaces 1064 and 308.

In an exemplary embodiment, ram assembly 122 can include a distal portion 1220 and a proximal portion 1222 separated by a feature 1224, such as a lip, a ledge, that can be configured to act as a seat for energy source 120. In an exemplary embodiment, compression spring 120 can be disposed between a proximal end of housing 102 and feature 1224. Distal portion 1220 can be substantially cylindrical and can be configured to concentrically receive at least a portion of sleeve 116 and guard 106. Distal portion 1220 can also include openings 1226 configured to receive legs 1170 of sleeve 116 and projection 1066 of guard 106.

Proximal portion 1222 preferably includes legs 1228, a ram 1232, and a trigger engagement member, such as, e.g., projections 1230. Although the trigger engagement member is shown as projections 1230, alternative implementations are contemplated. The trigger engagement member can include any feature (e.g., an elongated tab, a recess, a protrusion, a bulge, a thread, etc.) that can be held by ram retaining member in the pre-firing state, and released upon rotation of the floating trigger member. Camming surfaces 1064 and 308 are preferably oriented at an angle with respect to the longitudinal axis of the device to achieve a selected force and throw required to depress the guard 106 from the extended to the retracted position to fire the device. In some embodiments, the camming surfaces are angled at between 15° and 75° with respect to the axis, and more preferably between about 20° and 45°. In one embodiment, the camming surfaces are angles at about 30° with respect to the axis.

Figure 10B:
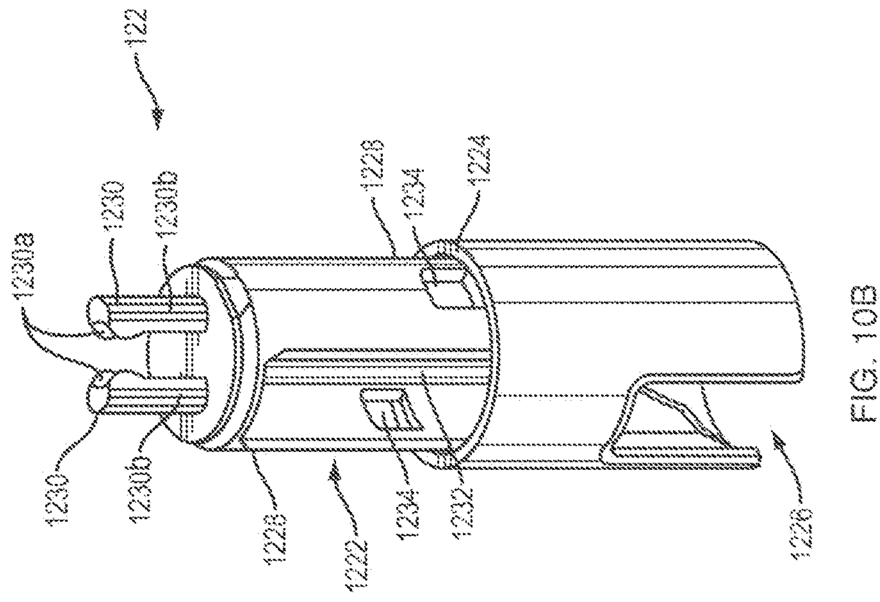
FIGS. 10A and 10B are side and perspective views respectively of a ram assembly of an exemplary injection device according to an exemplary embodiment of the present disclosure.
Figure 10A:
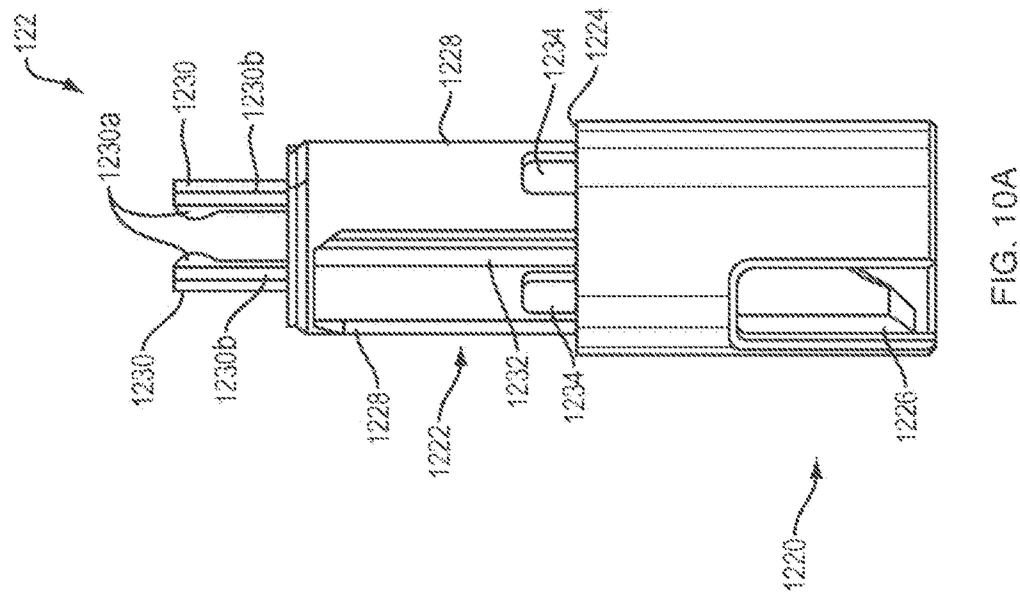
Figure 11:
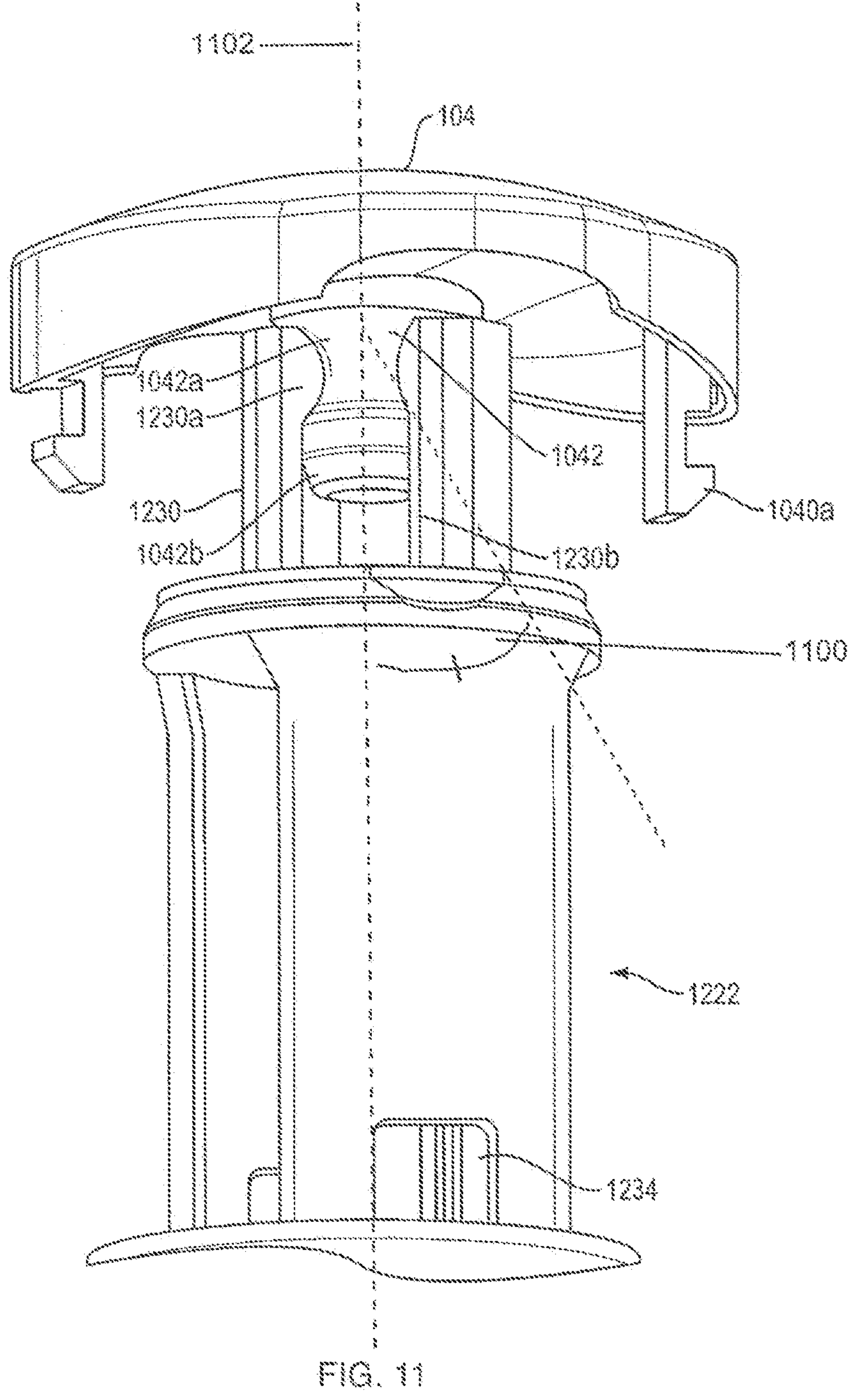
FIG. 11 shows a close-up view of an engagement of a trigger engagement member and a ram retaining member of an exemplary injection device according to an exemplary embodiment of the present disclosure.

As shown in FIGS. 10A and 10B, legs 1228 include openings 1234 configured to engage locking projections 1168 of sleeve 116. It is understood that openings 1234 accommodating alternate specific delivery volumes may be configured on 1220 to engage locking projections 1168 of sleeve 116. For example, locking projections 1168 of sleeve 116 can engage openings 1234 of firing mechanism 108 after injection device 100 has been fired, locking-out injection device 100 so that a user cannot initiate subsequent retraction of guard 106 exposing needle 112. Ram 1232 is configured to be in association with plunger 118, and distally displace plunger 118 under the force of energy source 120 to dispense the medicament contained in medicament chamber 110 during an injection. Additionally, projections 1230 can be disposed at a proximal end of proximal portion 1222 and can be configured to engage opening 302 of floating trigger member 300 and ram holding member 1042 of housing end/end cap 104. The engagement of projections 1230 with opening 302 and ram holding member 1042, as well as the alignment of projections 1230 within opening 302 can control and enable firing of injection device 100. For example, projections 1230 can include bulges 1230*a* configured to engage groove 1042*a* of ram holding member 1042, and shapes 1230*b* configured to engage bulge 1462*b* of ram holding member 1042. As noted above, projections 1230 and ram holding member 1042 preferably include circular cross-sections to allow rotation of floating trigger member 300 during firing of injection device 100. FIG. 11 shows a close-up view of the engagement of trigger engagement member (e.g., projections 1230) with ram holding member 1042.

In certain embodiments, the engagement of the ram holding member 1042 of housing end/end cap 104 with projections 1230 of ram assembly 122 creates a latch retention angle 1100. In one embodiment, latch retention angle 1100 is defined by axis 1102 and the contact surface of a distal portion of groove 1042*a* of ram holding member 1042 of housing end/end cap 104 and bulge 1230*a* of projections 1230 of ram assembly 122. In certain embodiments, projections 1230 and ram holding member 1042 are sized and shaped to create, when engaged, a latch retention angle 1100 of about 10°, about 11°, about 12°, about 13°, about 14°, about 15°, about 16°, about 17°, about 18°, about 19°, about 20°, about 21°, about 22°, about 23°, about 24°, about 25°, about 26°, about 27°, about 28°, about 29°, about 30°, about 31°, about 32°, about 33°, about 34°, about 35°, about 36°, about 37°, about 38°, about 39°, about 40°, about 41°, about 42°, about 43°, about 44°, about 45°, about 46°, about 47°, about 48°, about 49°, about 50°, about 51°, about 52°, about 53°, about 54°, about 55°, about 56°, about 57°, about 58°, about 59°, about 60°, about 61°, about 62°, about 63°, about 64°, about 65°, about 66°, about 67°, about 68°, about 69°, about 70°, about 71°, about 72°, about 73°, about 74°, about 75°, about 76°, about 77°, about 78°, about 79°, about 80°, about 81°, about 82°, about 83°, about 84°, about 85°, about 86°, about 87°, about 88°, about 89° or any range determinable from the preceding angles (for example, about 39° to about 41° or about 79° to about) 81°.

In an exemplary embodiment, the injection device 100 can be in a pre-firing "safeties-on" configuration. For example, in the pre-firing "safeties-on" configuration, injection device 100 is in a pre-firing state and cap 200 is affixed to injection device 100. In this configuration, guard 106 is in the extended position under force of spring 114 covering needle 112, ram assembly 122 is in its proximal position, and energy source 120 has not released its energy. Further, in this state, projections 1230 of ram assembly 122 are engaged with opening 302 of the floating trigger member 300 and aligned in the first position 302*a* (e.g., pre-firing condition) of opening 302. Further, projections 1230 are also engaged with ram holding member 1042 of housing end/end cap 104. In this position, the engagement of projections 1230 with ram holding member 1042 of housing end/end cap 104 oppose the force of energy source 120. Further, with projections 1230 aligned within the first position 302*a* of opening 302, the retaining portion 306 of opening 302 prevents projections 1230 from splaying open and disengaging ram holding member 1042 under the force of energy source 120.

In an exemplary embodiment, the injection device 100 can be in a pre-firing "ready-to-use" state. For example, in a pre-firing "ready-to-use" configuration, cap 200 has been removed, but the user has not otherwise initiated an injection. Accordingly, in this state, the medicament is still in medicament chamber 110, guard 106 remains in an extended position covering needle 112, energy source 120 has not released the energy that it has stored, and projections 1230 of ram assembly 122 remain engaged with ram holding member 1042 and aligned in the first position (302*a*) of opening 302 of floating trigger member.

In an exemplary embodiment, the injection device 100 can be in a triggered or "just-used" state. For example, in a triggered or "just-fired" state, guard 106 has been proximally slidably displaced (e.g., by application of a force on the distal end of guard 106) from the extended position to the retracted position, thereby exposing needle 112. Energy source 120 is just beginning to release its stored energy (e.g., the exemplary compression spring remains compressed), and ram assembly 122 remains in the proximal-most position. Injection device 100 may be in this state, for example, during an initial stage of use by a user. For example, this can be observed when the user has pressed guard 106 of injection device 100 against an injection site to perform an injection. Accordingly, the force exerted by the user in pressing guard 106 of injection device 100 against the injection site may have proximally displaced guard 106 against the force of spring 114, thereby displacing guard 106 into the retracted position and exposing needle 112 to penetrate the user's skin at the injection site.

In this triggered state, guard 106 has been displaced into the retracted position, camming surfaces 1064 of guard 106 engage camming surfaces 308 of floating trigger member 300, thereby camming floating trigger member 300. This camming action rotates floating trigger member 300, causing projections 1230 to become unaligned with the first position of opening 302 and become aligned with the second position of opening 302. In this position, projections 1230 are no longer restrained from splaying open by retaining portion 306 of opening 302. Accordingly, projections 1230 splay open under the force of, energy source 120, causing projections 1230 to disengage with ram holding member 1042 of housing end/end cap 104. The disengagement of projections 1230 with ram holding member 1042 allows ram assembly 122 to be distally slidably displaced relative to housing 102 under the force generated by energy source 120. The distal displacement of ram assembly 120 is preferably restrained by ram assembly 120 abutting a proximal surface of ring-like structure 1160 of sleeve 116.

In an exemplary embodiment, the injection device 100 can be in a "just-injected" state. This state follows the disengagement of projections 1230 with ram holding member 1042 and the distal displacement of ram assembly 122 described above. In this state, energy source 120 (e.g., a compression spring) has released its energy, thereby distally displacing ram assembly 122. Further, guard 106 remains compressed in the retracted position. This state may be observed during use of injection device 100 immediately following the trigger or "just-used" state. As described above, camming of floating trigger member 300 aligns projections 1230 with the second position defined by opening 302, allowing projections 1230 to splay open and disengage ram holding member 1042 under the force released by energy source 120. Accordingly, energy source 120 has released at least some, if not all, of its stored energy (e.g., compression spring is less compressed), and ram assembly 122, as well as ram 1232, has been distally displaced into a distal position. The distal displacement of ram 1232 urges plunger 118 in a distal direction, injecting the medicament into the user by dispensing the medicament in medicament chamber 110 through needle 112 and into the user. Although the injection has preferably been completed in this state, injection device 100 is still likely pressed against the injection site since guard 106 remains in a retracted position exposing needle 112. Further, this distal displacement of ram assembly 122 preferably positions ram assembly 122 such that it is displayed in a window of housing 102. In an exemplary embodiment, after the distal displacement of ram assembly 122, it is disposed between medicament container 110 and housing 102 such that it is entirely occluding the window so that only ram assembly 122 is visible through the window, and medicament container 110 is no longer visible (e.g., ram assembly is disposed between medicament container 110 and the window). Further, ram assembly 122 can have a color (as described above) that would be a clear indicator to a user that injection device 100 has been used, and different than the other colors visible from the outside of the injector before firing.

In an exemplary embodiment, the injection device can be in a "locked-out" state. For example, the "locked-out" state can be observed after the user has removed injection device 100 from the injection site. In this state, nothing is restraining guard 106 in the retracted position against the force of spring 114, and accordingly, guard 106 is distally displaced from the retracted position to the extended position under the force of spring 114, thereby covering needle 112. As guard 106 moves distally from the retracted position to the extended position under the force of spring 114, projections 1066, which are disposed on springs 1068 biased in an outward direction, engage and openings created between proximal surfaces of legs 1170 of sleeve 116 and proximal walls of openings 1226. Accordingly, the association of projections 1066 with the proximal walls of openings 1226 prevents guard 106 from being displaced proximally, and the association of projections 1066 with the proximal surfaces of legs 1170 prevents guard 106 from being displaced distally. Thus, guard 106 is in a locked position, thereby "locking-out" injection device 100 such that needle 112 is covered and guard 106 is locked in place so that a user cannot attempt a subsequent injection. Afterwards, the user may affix cap 200 back onto the distal end of injection device 100.

Advantageously, this "locked-out" state is preferably not dependent on displacement of guard 106, but rather, is preferably dependent on dispensing of the medicament stored in medicament chamber 110 and/or movement of ram assembly 122. For example, injection device 100 becomes locked-out in situations where the medicament is inadvertently dispensed, even if guard 106 has not been displaced. Injection device 100 can become locked-out in any instance where energy source 120 is activated and ram assembly 122 is distally displaced, causing ram 1232 to displace plunger 118, thereby dispensing the medicament in medicament chamber 110.

Figure 12:
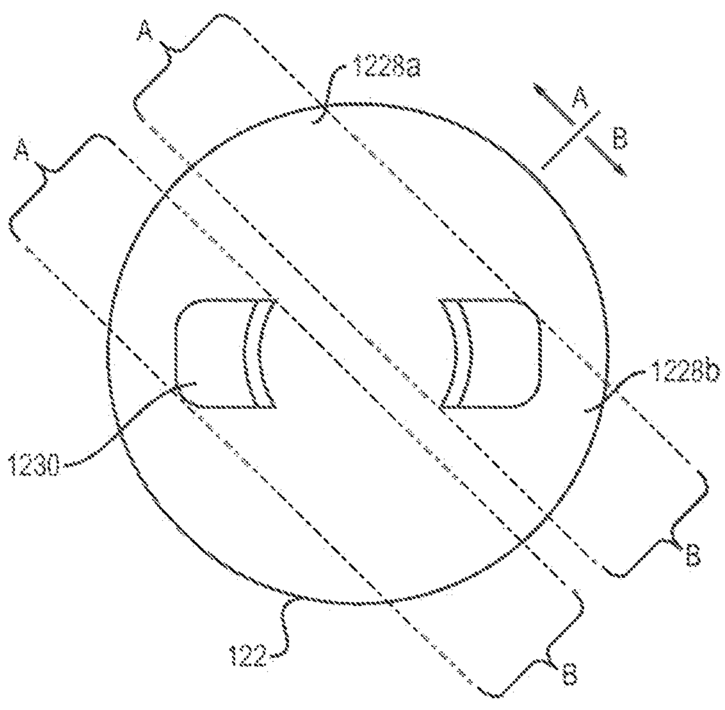
FIG. 12 shows a top view of a ram assembly of an exemplary injection device according to an exemplary embodiment of the present disclosure.
Figure 13:
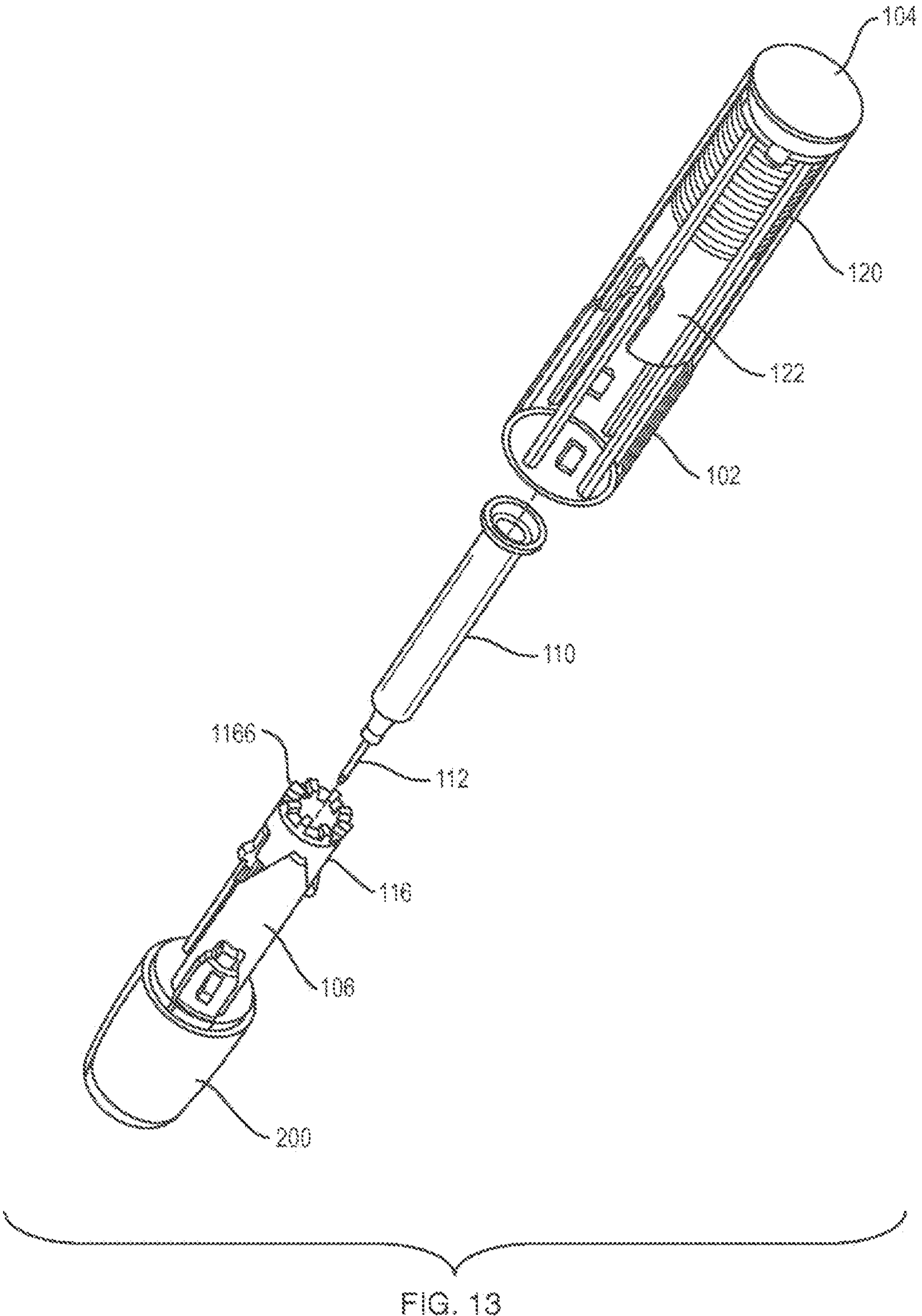
FIG. 13 is an exploded view of an exemplary injection device according to an exemplary embodiment of the present disclosure.

In an exemplary embodiment, many of the components of injection device 100 are preferably made of a resilient plastic or polymer, or a metal. Preferably, projections 1230 of ram assembly 122 are oriented so that ram assembly 122 can be molded using a single mold. For example, as shown in FIG. 10, projections 1230 (which are preferably concentrically symmetrical to each other) can be aligned at an angle relative to the alignment of the other features of ram assembly 122, such as legs 1228 (which are preferably concentrically symmetrical to each other). For example, as shown in FIG. 12, a single mold can form the portion of ram assembly 120 designated A (including all the features, components, openings, etc. 1228A), and a single mold can form the portion of ram assembly designated B (including all the features, components, openings, etc. 1228B). Thus, each surface of projections 1230 is preferably accessible along a direction of separating the two molds, and the two molds can be separated linearly without a concave portion of projections 1230 facing orthogonal to the separation direction impeding separation and removal of the molds.

Further, cap 200 can be configured helically so that it can be molded without a hole/opening. For example, cap 200 can include threads 206 that permit cap 200 to be threadedly removed from a mold. Further, outer housing 102 can include a translucent material to allow users to view the inner workings of injection device 100, and ascertain if it is malfunctioning (e.g., as shown in FIG. 1). Additionally, injection device 100 can include various gripping elements, such as ridges, pads, contours, or the like, to make injection device 100 more ergonomic, easy to use, and comfortable to the user. Further, injection device 100 can include markings, such as a sticker, brand markings, drug information, numerals, arrows, or the like, to indicate the steps needed to perform an injection, and areas for promotional markings such as brand and logo designations.

While illustrative embodiments of the invention are disclosed herein, it will be appreciated that numerous modifications and other embodiments may be devised by those skilled in the art. For example, the features for the various embodiments can be used in other embodiments. Other embodiments can include different mechanisms to cause the rotation of the floating trigger member 300 to release the projections 1230 from the opening 302, such as by direct rotation of the floating trigger member 300 by a user, such as via a slide or other element accessible on the outside of the housing, or by a button that is pushed with a finger, or another transmission mechanism to rotate the floating trigger member. Therefore, it will be understood that the appended claims are intended to cover all such modifications and embodiments that come within the spirit and scope of the present invention.

Each and every reference herein is incorporated by reference in its entirety. The entire disclosure of U.S. Pat. Nos. 8,021,335, 7,776,015, and 6,391,003, U.S. patent application Ser. No. 13/184,229 and U.S. provisional patent application No. 61/621,298 are hereby incorporated herein by reference thereto as if fully set forth herein. The term "about," as used herein, should generally be understood to refer to both the corresponding number and a range of numbers. Moreover, all numerical ranges herein should be understood to include each whole integer within the range.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The invention claimed is:

1. A method for delivering a medicament to a subject in need thereof, the method comprising injecting the medicament in the subject using an injector comprising:

a housing;

a trigger mechanism including:

- a floating trigger member having a retaining portion; and
- a ram assembly slidably mounted within the housing and having a ram defining an axis and configured to pressurize a medicament container for expelling the medicament therefrom, the ram assembly further having a floating trigger engagement member configured to engage the retaining portion of the floating trigger member when the floating trigger member is in a pre-firing condition;

an energy source associated with the ram for powering the ram to expel the medicament; and a user-operable firing-initiation member operable for causing a rotation of the floating trigger member about the axis from the pre-firing condition to a firing condition in which the floating trigger engagement member is released from the retaining portion to allow the energy source to fire the ram.

2. The method of claim 1, wherein the energy source is configured to pressurize the medicament to between about 80 psi and about 1000 psi.

3. The method of claim 1, wherein a needle is in fluid communication with the medicament container for injecting the medicament expelled therefrom during a firing.

4. The method of claim 3, wherein the energy source and the needle are configured for jet injecting the medicament through the needle.

5. The method of claim 3, wherein the energy source and the needle are configured for injecting the medicament at a rate of between 0.2 mL/sec and about 0.75 mL/sec.

6. The method of claim 5, wherein the energy source and the needle are configured for injecting the medicament at a rate of about 0.2 mL/sec.

7. The method of claim 6, wherein the energy source and the needle are configured for injecting the medicament at a rate of about 4 mL/sec.

8. The method of claim 3, wherein the needle has a length of between about 4 mm and about 8 mm.

9. The method of claim 3, wherein the needle is a 26-28 gauge needle.

10. The method of claim 1, wherein about 0.2 mL to about 4 mL of medicament is delivered.

11. The method of claim 1, wherein the energy source is configured for powering the ram with a force of about 10 pounds to about 15 pounds.

12. The method of claim 1, wherein the medicament comprises an androgen.

13. The method of claim 12, wherein the androgen includes testosterone or a derivative or ester thereof.

14. The method of claim 13, wherein the androgen includes testosterone cypionate.

15. The method of claim 14, wherein the androgen includes testosterone enanthate.

16. A method for delivering a medicament to a subject in need thereof, the method comprising injecting the medicament in the subject using an injector comprising:

a housing;

a trigger mechanism including:

a floating trigger member having a retaining portion; and a ram assembly slidably mounted within the housing and having a ram defining an axis and configured to pressurize a medicament container for expelling the medicament therefrom, the ram assembly further having a floating trigger engagement member configured to engage the retaining portion of the floating trigger member when the floating trigger member is in a pre-firing condition;

an energy source associated with the ram for powering the ram to expel the medicament; and a user-operable firing-initiation member operable for causing a rotation of the floating trigger member about the axis from the pre-firing condition to a firing condition in which the floating trigger engagement member is released from the retaining portion to allow the energy source to fire the ram, wherein the energy source is configured to pressurize the medicament to between about 80 psi and about 1000 psi, wherein the energy source and the needle are configured for injecting the medicament at a rate of between 0.2 mL/sec and about 0.75 mL/sec, wherein about 0.2 mL to about 4 mL of medicament is delivered, wherein the needle has a length of between about 4 mm and about 8 mm, and wherein the energy source is configured for powering the ram with a force of about 10 pounds to about 15 pounds.

* * * * *